US005885571A

United States Patent [19]

Lambert et al.

[11] Patent Number: 5,885,571

[45] Date of Patent: Mar. 23, 1999

[54] *BACILLUS THURINGIENSIS* STRAINS AND THEIR INSECTICIDAL PROTEINS

[75] Inventors: Bart Lambert, Beernem; Stefan Jansens, Ghent; Katrien Van Audenhove, Brugge; Marnix Peferoen, Nevele, all of Belgium

[73] Assignee: Plant Genetic Systems, N.V., Brussles, Belgium

[21] Appl. No.: 379,656

[22] PCT Filed: Jul. 12, 1993

[86] PCT No.: PCT/EP93/01820

§ 371 Date: Mar. 23, 1995

§ 102(e) Date: Mar. 23, 1995

[87] PCT Pub. No.: WO94/05771

PCT Pub. Date: Mar. 17, 1994

[30] Foreign Application Priority Data

Aug. 27, 1992 [EP] European Pat. Off. .............. 92402358
Apr. 9, 1993 [EP] European Pat. Off. .............. 93400949

[51] Int. Cl.$^6$ ........................ A01N 63/02; C07K 14/325; C12N 15/32; C12N 1/21

[52] U.S. Cl. .................................. 424/93.461; 435/252.5; 435/252.3; 435/252.31; 435/320.1; 435/71.3; 536/28.1; 536/28.71; 514/12; 424/93.2

[58] Field of Search .............................. 435/252.5, 252.3, 435/252.31, 320.1, 71.3, 419; 536/23.1, 23.71; 514/12; 424/93.2, 93.461; 800/205

[56] References Cited

FOREIGN PATENT DOCUMENTS 0358557 3/1990 European Pat. Off. .
0498537 8/1992 European Pat. Off. .
9006999 6/1990 WIPO .
9304587 3/1993 WIPO .

OTHER PUBLICATIONS

Gleave et al., J. General Microbiology, 138, 55–62 (1992).

Smulevitch et al., FEBS Letters, 298, 25–28 (1991).

Vaeck et al., Nature, 328, 33–37 (1987).

Hofte et al., Microbiological Reviews, 53, 242–255 (1989).

H. Wabiko et al., "*Bacillus thuringiensis* Entomocidal Protoxin Gene Sequence and gene Product Analysis", DNA 5(4): 305–314, 1986.

*Primary Examiner*—Rebecca E. Prouty
*Attorney, Agent, or Firm*—Birch, Stewart, Kolasch & Birch, LLP

[57] ABSTRACT

Four novel *Bacillus thurungienisis* strains which are deposited at the BCCM-LMG under accesion nos. LMG P-12592, LMG P-12593, LMG P-12594, and LMG P-13493, produce new crystal proteins during sporulation that are toxic to Lepidoptera, more particularly against Noctuidae such as Spodoptera spp. and *Agrotis ipsilon,* against Pyralidae such as *Ostrinia nubilalis,* and against Yponomeutidae such as *Plutella xylostella,* and that are encoded by a novel gene. The crystal proteins contain protoxins, which can yield a toxin as trypsin-digestion product. A plant, the genome of which is transformed with a DNA sequence that comes from either one of the strains and that encodes its respective toxin, is resistant to Lepidoptera. Each strain, itself, or its crystals, crystals proteins, protoxin or toxin can be used as the active ingredient in an insecticidal composition for combatting Lepidoptera.

23 Claims, 1 Drawing Sheet

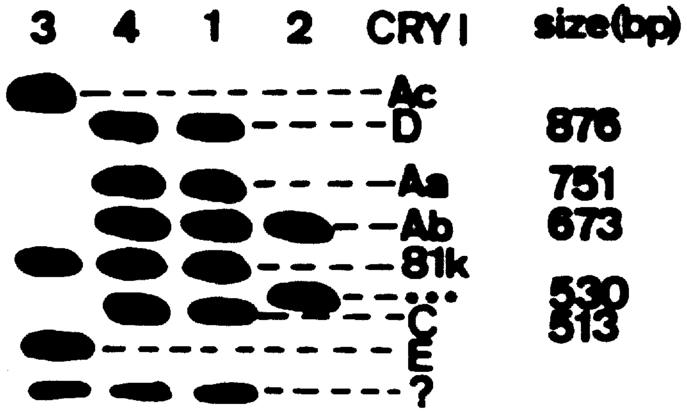
3 4 1 2 CRYI
size(bp)
Ac
D
876
Aa
751
Ab
673
81k
530
C
513
E
?

*BACILLUS THURINGIENSIS* STRAINS AND THEIR INSECTICIDAL PROTEINS

This invention relates to four novel strains of *Bacillus thuringiensis* (the "BTS02617A strain", the "BTS02618A strain", the "BTS02654B strain" and the "BTS02652E strain"), each of which produces crystallized proteins (the "BTS02617A crystal proteins", the "BTS02618A crystal proteins", the "BTS02654B crystal proteins" and the "BTS02652E crystal proteins", respectively) which are packaged in crystals (the "BTS02617A crystals", the "BTS02618A crystals", the "BTS02654B crystals" and the "BTS02652E crystals", respectively) during sporulation. The BTS02617A, BTS02618A, BTS02654B and BTS02652E strains were deposited under the provisions of the Budapest Treaty at the Belgian Coordinated Collections of Microorganisms—Collection Laboratorium voor Microbiologie Belgium ("BCCM-LMG"), R.U.G., K. Ledeganckstraat 35, B-9000 Gent.

This invention also relates to an insecticide composition that is active against Lepidoptera and that comprises the BTS02617A, BTS02618A, BTS02654B or BTS02652E strain, as such, or preferably the BTS02617A, BTS02618A, BTS02654B or BTS02652E crystals, crystal proteins or the active component(s) thereof as an active ingredient.

This invention further relates to a gene (the "bTS02618A gene"), which is present in the genome of the BTS02617A, BTS02618A, BTS02654B and BTS02652E strains and which encodes an insecticidal protein (the "BTS02618A protoxin") that is found in the BTS02617A, BTS02618A, BTS02654B and BTS02652E crystals. The BTS02618A protoxin is the protein that is produced by the BTS02617A, BTS02618A, BTS02654B and BTS02652E strains before being packaged into their respective BTS02617A, BTS02618A, BTS02654B and BTS02652E crystals.

This invention still further relates to a toxin (the "BTS02618A toxin") which can be obtained (e.g., by trypsin digestion) from the BTS02618A protoxin. The BTS02618A toxin is an insecticidally active protein which can be liberated from the BTS02617A crystals, the BTS02618A crystals, the BTS02654B crystals, and the BTS02652E crystals, which are produced by the BTS02617A strain, the BTS02618A strain, the BTS02654B strain and the BTS02652E strain, respectively. This toxin and its protoxin have a high activity against a wide range of lepidopteran insects, particularly against Noctuidae, especially against Spodoptera and Agrotis spp., but also against other important lepidopteran insects such as Pyralidae, particularly the European corn borer, *Ostrinia nubilalis*, and Yponomeutidae such as *Plutella xylostella*. This new characteristic of the BTS02618A protoxin and toxin ("(pro)toxin"), i.e., the combination of activity against different economically important Lepidopteran insect families such as Noctuidae, Yponomeutidae and Pyralidae, makes this (pro)toxin an ideally suited compound for combatting a wide range of insect pests by contacting these insects with the (pro)toxin, e.g., by spraying or by expressing the bTS02618A gene in plant-associated bacteria or in plants. The BTS02618A toxin is believed to represent the smallest portion of the BTS02618A protoxin which is insecticidally effective against Lepidoptera.

This invention yet further relates to a chimeric gene that can be used to transform a plant cell and that contains the following operably linked DNA fragments:

1) a part of the bTS02618A gene (the "insecticidally effective bTS02618A gene part") encoding an insecticidally effective portion of the BTS02618A protoxin, preferably a truncated part of the bTS02618A gene (the "truncated bTS02618A gene") encoding just the BTS02618A toxin;
2) a promoter suitable for transcription of the insecticidally effective bTS02618A gene part in a plant cell; and
3) suitable 3' end transcript formation and polyadenylation signals for expressing the insecticidally effective bTS02618A gene part in a plant cell.

This chimeric gene is hereinafter generally referred to as the "bTS02618A chimeric gene".

This invention also relates to:

1) a cell (the "transformed plant cell") of a plant, such as corn or cotton, the genome of which is transformed with the insecticidally effective bTS02618A gene part, preferably the bTS02618A chimeric gene; and
2) a plant (the "transformed plant") which is regenerated from the transformed plant cell or is produced from the so-regenerated plant and their seeds, the genome of which contains the insecticidally effective bTS02618A gene part, preferably the bTS02618A chimeric gene, and which is resistant to Lepidoptera.

This invention still further relates to:

1) a microbial organism, such as *B. thuringiensis* or Pseudomonas spp., the genome of which is transformed with all or part of the bTS02618A gene; and
2) a microbial spore, containing a genome which is transformed with all or parts of the bTS02618A gene.

BACKGROUND OF THE INVENTION

*B. thuringiensis* ("Bt") is a Gram-positive bacterium which produces endogenous crystals upon sporulation. The crystals are composed of proteins which are specifically toxic against insect larvae. These crystal proteins and corresponding genes have been classified based on their structure and insecticidal spectrum (Höfte and Whiteley, 1989). The four major classes are Lepidoptera-specific (cryI), Lepidoptera- and Diptera-specific (cryII), Coleoptera-specific (cryIII), and Diptera-specific (cryIV) genes.

The fact that conventional submerged fermentation techniques can be used to produce Bt spores on a large scale makes Bt bacteria commercially attractive as a source of insecticidal compositions.

Gene fragments from some Bt strains, encoding insecticidal proteins, have heretofore been identified and integrated into plant genomes in order to render the plants insect-resistant. However, obtaining expression of such Bt gene fragments in plants is not a straightforward process. In order to achieve optimal expression of an insecticidal protein in plant cells, it has been found necessary to engineer each Bt gene fragment in a specific way so that it encodes a part of a Bt protoxin that retains substantial toxicity against its target insects (European patent application ("EPA") 86/300,291.1 and 88/402,115.5; U.S. patent application Ser. No. 821,582, filed Jan. 22, 1986).

SUMMARY OF THE INVENTION

In accordance with this invention, four novel Bt strains, i.e., the BTS02617A, BTS02618A, BTS02654B and BTS02652E strains, are provided. The BTS02617A, BTS02618A, BTS02654B and BTS02652E crystals and crystal proteins, the BTS02618A protoxin and toxin produced by the strains during sporulation, and insecticidally effective portions of the BTS02618A protoxin, as well as equivalents of these crystals, crystal proteins, protoxin, toxin and insecticidally effective protoxin portions, each possess insecticidal activity and can therefore be formulated into insecticidal compositions against Lepidoptera in general, and particularly against Noctuidae, such as Agrotis spp. (cutworms such as *Agrotis ipsilon*), Mamestra spp. (e.g., the cabbage moth, *Mamestra brassica*) and Spodoptera spp. (armyworms, such as *Spodoptera exigua, Spodoptera frugiperda, Spodoptera littoralis* and *Spodoptera litura*), against Pyralidae (e.g., the European corn borer, *Ostrinia nubilalis*) and Yponomeutidae (such as *Plutella xylostella*) which are major pests of various economically important crops, such as corn, cotton and many vegetables such as Brassicas.

Also in accordance with this invention, a plant cell genome is transformed with the insecticidally effective bTS02618A gene part, preferably the truncated bTS02618A gene, or an equivalent thereof such as a modified, synthetic bTS02618A gene. It is preferred that this transformation be carried out with the bTS02618A chimeric gene. The resulting transformed plant cell can be used to produce transformed plants, seeds of transformed plants and plant cell cultures consisting essentially of the transformed cells. The transformed cells in some or all of the tissues of the transformed plants: 1) contain the insecticidally effective bTS02618A gene part as a stable insert in their genome, and 2) express the insecticidally effective bTS02618A gene part by producing an insecticidally effective portion of its BTS02618A protoxin, preferably its BTS02618A toxin, thereby rendering the plant resistant to Lepidoptera. The transformed plant cells of this invention can also be used to produce, for recovery, such insecticidal Bt proteins.

Further in accordance with this invention, a process is provided for rendering a plant resistant to Lepidoptera by transforming the plant cell genome with the insecticidally effective bTS02618A gene part, preferably the truncated bTS02618A gene, or an equivalent thereof. In this regard, it is preferred that the plant cell be transformed with the bTS02618A chimeric gene.

Yet further in accordance with this invention, there are provided the BTS02618A protoxin, the insecticidally effective portions of such protoxin and the BTS02618A toxin, as well as functional parts of the BTS02618A toxin, as well as the bTS02618A gene, the insecticidally effective bTS02618A gene part, the truncated bTS02618A gene and the chimeric bTS02618A gene, as well as their equivalents.

Also in accordance with this invention, a DNA sequence, either natural or artificial, encoding the BTS02618A protoxin or insecticidally effective portions thereof, such as the toxin, is provided.

Also in accordance with this invention are provided an insecticidal composition against Lepidoptera, particularly Noctuidae, Pyralidae and Yponomeutidae, and a method for controlling Lepidoptera, particularly Noctuidae, Pyralidae and Yponomeutidae, with the insecticidal composition, wherein the insecticidal composition comprises the BTS02617A, BTS02618A, BTS02654B or BTS02652E strain, crystals and/or crystal proteins or the BTS02618A protoxin, toxin and/or insecticidally effective protoxin portions or their equivalents.

DETAILED DESCRIPTION OF THE INVENTION

The BTS02618A protoxin of this invention can be isolated in a conventional manner from the BTS02617A strain, deposited on July 2 at the BCCM-LMG under accession number LMG P-12592, the BTS02618A strain, deposited on Jul. 2, 1992 at the BCCM-LMG under accession number LMG P-12593, the BTS02654B strain, deposited on Jul. 2, 1992 at the BCCM-LMG under accession number LMG P-12594, or the BTS02652E strain deposited on Mar. 1, 1993 at the BCCM-LMG under accession number LMG P-13493. For example, the BTS02617A, BTS02618A, BTS02654B or BTS02652E crystals can be isolated from sporulated cultures of their respective strain (Mahillon and Delcour, 1984), and then, the BTS02618A protoxin can be isolated from the crystals according to the method of Höfte et al. (1986). The protoxins can be used to prepare monoclonal or polyclonal antibodies specific for the protoxin in a conventional manner (Höfte et al., 1988). The BTS02618A toxin can be obtained by protease (e.g., trypsin) digestion of the BTS02618A protoxin.

The bTS02618A gene can be isolated in a conventional manner. The bTS02618A gene can be identified in the BTS02617A, BTS02618A, BTS02654B or BTS02652E strain, using the procedure described in U.S. patent application Ser. No. 821,582, filed Jan. 22, 1986, and in EPA 86/300,291.1 and 88/402,115.5 (which are incorporated herein by reference). The bTS02618A gene was identified by: digesting total DNA from one of the above strains with restriction enzymes; size fractionating the DNA fragments, so produced, into DNA fractions of 5 to 10 Kb; ligating these fractions to cloning vectors; screening the *E. coli*, transformed with the cloning vectors, with a DNA probe that was constructed from a region of the cryIG gene (Smulevitch et al., 1991; Gleave et al., 1992).

The term “bTS02618A gene” as used herein includes a DNA sequence encoding the BTS02618A protoxin or toxin or functionally equivalent variants thereof. Indeed, because of the degeneracy of the genetic code, some amino acid codons can be replaced with others without changing the amino acid sequence of the protein. Furthermore, some amino acids can be substituted by other equivalent amino acids without significantly changing the insecticidal activity of the protein. Also, changes in amino acid composition in regions of the molecule, different from those responsible for binding and toxicity are less likely to cause a difference in insecticidal activity of the protein. Such equivalents of the gene include DNA sequences hybridizing to the DNA sequence of the BTS02618A toxin or protoxin of SEQ ID. No. 4 and encoding a protein with the same insecticidal characteristics as the BTS02618A (pro)toxin, of this invention. In this context, the term “hybridization” refers to conventional hybridization conditions, most preferably stringent hybridization conditions.

The term “functional parts of the BTS02618A toxin” as used herein means any part(s) or domain(s) of the toxin with a specific structure that can be transferred to another (Bt) protein for providing a new hybrid protein with at least one functional characteristic (e.g., the binding and/or toxicity characteristics) of the BTS02618A toxin (Ge et al., 1991). Such parts can form an essential feature of the hybrid Bt protein with the binding and/or toxicity characteristics of the BTS02618A protein. Such a hybrid protein can have an enlarged host range, an improved toxicity and/or can be used in a strategy to prevent insect resistance development (European Patent Publication (“EP”) 408 403; Visser et al., 1993).

Alternatively, the 5 to 10 Kb fragments, prepared from total DNA of the BTS02617A or BTS02618A or BTS02654B or BTS02652E strain, can be ligated in suitable expression vectors and transformed in *E. coli*, and the clones can then be screened by conventional colony immunoprobing methods (French et al., 1986) for expression of the toxin with monoclonal or polyclonal antibodies raised against the BTS02618A toxin.

Also, the 5 to 10 Kb fragments, prepared from total DNA of the BTS02617A or BTS02618A or BTS02654B or BTS02652E strain, can be ligated in suitable Bt shuttle vectors (Lereclus et al., 1992) and transformed in a crystal minus Bt-mutant. The clones are then screened for production of crystals (detected by microscopy) or crystal proteins (detected by SDS-PAGE).

The so-identified bTS02618A gene was sequenced in a conventional manner (Maxam and Gilbert, 1980) to obtain the DNA sequence. Hybridization in Southern blots and sequence comparison indicated that this gene is different from previously described genes encoding protoxins and toxins with activity against Lepidoptera (Höfte and Whiteley, 1989).

An insecticidally effective part of the bTS02618A gene, encoding an insecticidally effective portion of its protoxin, and a truncated part of the gene, encoding just its toxin, can be made in a conventional manner after sequence analysis of the gene. The amino acid sequence of the BTS02618A protoxin and toxin was determined from the DNA sequence of the bTS02618A gene and the truncated bTS02618A gene. By "an insecticidally effective part" or "a part" of the bTS02618A gene is meant a DNA sequence encoding a polypeptide which has fewer amino acids than the BTS02618A protoxin but which is still toxic to Lepidoptera.

In order to express all or an insecticidally effective part of the bTS02618A gene or an equivalent gene in *E. coli*, in other Bt strains and in plants, suitable restriction sites can be introduced, flanking each gene or gene part. This can be done by site-directed mutagenesis, using well-known procedures (Stanssens et al., 1989; White et al., 1989). In order to obtain improved expression in plants, it may be preferred to modify the codon usage of the bTS02618A gene or insecticidally effective bTS02618A gene part to form an equivalent, modified or artificial gene or gene part in accordance with PCT publications WO 91/16432 and WO 93/09218; EP 0,358,962 and EP 0,359,472. For obtaining enhanced expression in monocot plants such as corn, a monocot intron also can be added to the bTS02618A chimeric gene, and the DNA sequence of the bTS02618A gene part can be further changed in a translationally neutral manner, to modify possibly inhibiting DNA sequences present in the gene part by means of site-directed intron insertion and/or by introducing changes to the codon usage, e.g., adapting the codon usage to that most preferred by the specific plant (Murray et al., 1989) without changing significantly the encoded amino acid sequence.

The insecticidally effective bTS02618A gene part or its equivalent, preferably the bTS02618A chimeric gene, encoding an insecticidally effective portion of the BTS02618A protoxin, can be stably inserted in a conventional manner into the nuclear genome of a single plant cell, and the so-transformed plant cell can be used in a conventional manner to produce a transformed plant that is insect-resistant. In this regard, a disarmed Ti-plasmid, containing the insecticidally effective bTS02618A gene part, in *Agrobacterium tumefaciens* can be used to transform the plant cell, and thereafter, a transformed plant can be regenerated from the transformed plant cell using the procedures described, for example, in EP 0,116,718, EP 0,270,822, PCT publication WO 84/02,913 and European Patent Application ("EPA") 87/400,544.0 (which are also incorporated herein by reference), and in Gould et al. (1991). Preferred Ti-plasmid vectors each contain the insecticidally effective bTS02618A gene part between the border sequences, or at least located to the left of the right border sequence, of the T-DNA of the Ti-plasmid. Of course, other types of vectors can be used to transform the plant cell, using procedures such as direct gene transfer (as described, for example in EP 0,233,247), pollen mediated transformation (as described, for example in EP 0,270,356, PCT publication WO 85/01856, and U.S. Pat. No. 4,684,611), plant RNA virus-mediated transformation (as described, for example in EP 0,067,553 and U.S. Pat. No. 4,407,956), liposome-mediated transformation (as described, for example in U.S. Pat. No. 4,536,475), and other methods such as the recently described methods for transforming certain lines of corn (Fromm et al., 1990; Gordon-Kamm et al., 1990) and rice (Shimamoto et al., 1989; Datta et al., 1990) and the recently described method for transforming monocots generally (PCT publication WO 92/09696).

The resulting transformed plant can be used in a conventional plant breeding scheme to produce more transformed plants with the same characteristics or to introduce the insecticidally effective bTS02618A gene part in other varieties of the same or related plant species. Seeds, which are obtained from the transformed plants, contain the insecticidally effective bTS02618A gene part as a stable genomic insert. Cells of the transformed plant can be cultured in a conventional manner to produce the insecticidally effective portion of the BTS02618A protoxin, preferably the BTS02618A toxin, which can be recovered for use in conventional insecticide compositions against Lepidoptera (U.S. patent application Ser. No. 821,582; EPA 86/300291.1.).

The insecticidally effective bTS02618A gene part, preferably the truncated bTS02618A gene, is inserted in a plant cell genome so that the inserted gene is downstream (i.e., 3') of, and under the control of, a promoter which can direct the expression of the gene part in the plant cell. This is preferably accomplished by inserting the bTS02618A chimeric gene in the plant cell genome. Preferred promoters include: the strong constitutive 35S promoters (the "35S promoters") of the cauliflower mosaic virus of isolates CM 1841 (Gardner et al., 1981), CabbB-S (Franck et al., 1980) and CabbB-JI (Hull and Howell, 1987); and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted bTS02618A gene part is expressed only in cells of the specific tissue(s) or organ(s). For example, the insecticidally effective bTS02618A gene part could be selectively expressed in the leaves of a plant (e.g., corn, cotton) by placing the insecticidally effective gene part under the control of a light-inducible promoter such as the promoter of the ribulose-1,5-bisphosphate carboxylase small subunit gene of the plant itself or of another plant such as pea as disclosed in U.S. patent application Ser. No. 821,582 and EPA 86/300,291.1. Another alternative is to use a promoter whose expression is inducible (e.g., by temperature or chemical factors).

The insecticidally effective bTS02618A gene part is inserted in the plant genome so that the inserted gene part is upstream (i.e., 5') of suitable 3' end transcription regulation signals (i.e., transcript formation and polyadenylation signals). This is preferably accomplished by inserting the bTS02618A chimeric gene in the plant cell genome. Preferred polyadenylation and transcript formation signals include those of the octopine synthase gene (Gielen et al., 1984) and the T-DNA gene 7 (Velten and Schell, 1985), which act as 3' -untranslated DNA sequences in transformed plant cells.

The insecticidally effective bTS02618A gene part can optionally be inserted in the plant genome as a hybrid gene (EPA 86/300,291.1; Vaeck et al., 1987) under the control of the same promoter as a selectable marker gene, such as the neo gene (EP 0,242,236) encoding kanamycin resistance, so that the plant expresses a fusion protein.

All or part of the bTS02618A gene, encoding an anti-lepidopteran protein, can also be used to transform other bacteria, such as a *B. thuringiensis* which has insecticidal activity against Lepidoptera or Coleoptera. Thereby, a transformed Bt strain can be produced which is useful for combatting a wide spectrum of lepidopteran and coleopteran insect pests or for combatting additional lepidopteran insect pests. Transformation of bacteria with all or part of the bTS02618A gene, incorporated in a suitable cloning vehicle, can be carried out in a conventional manner, preferably using conventional electroporation techniques as described in Mahillon et al. (1989) and in PCT Patent publication WO 90/06999.

The BTS02617A, BTS02618A, BTS02654B or BTS02652E strain also can be transformed with all or an insecticidally effective part of one or more foreign Bt genes such as: the bt18 gene (EP 0,358,557) or another Bt gene coding for an anti-Lepidoptera protein; and the bt109P gene (PCT publication WO 91/16433), coding for an anti-Coleoptera protein. Thereby, a transformed Bt strain can be produced which is useful for combatting an even greater variety of insect pests (e.g., Coleoptera and/or additional Lepidoptera).

Transformation of the BTS02617A, BTS02618A, BTS02654B or BTS02652E strain with all or part of a foreign Bt gene, incorporated in a conventional cloning vector, can be carried out in a well known manner, preferably using conventional electroporation techniques (Chassy et al., 1988) or other methods, e.g., as described by Lereclus et al. (1992).

Each of the BTS02617A, BTS02618A, BTS02654B or BTS02652E strains can be fermented by conventional methods (Dulmage, 1981; Bernhard and Utz, 1993) to provide high yields of cells. Under appropriate conditions which are well understood (Dulmage, 1981), the BTS02617A, BTS02618A, BTS02654B and BTS02652E strains each sporulate to produce crystal proteins containing the BTS02168A protoxin in high yields.

An insecticidal, particularly anti-lepidopteran, composition of this invention can be formulated in a conventional manner using the BTS02617A, BTS02618A, BTS02654B or BTS02652E strain or preferably their respective crystals, crystal proteins or the BTS02168A protoxin, toxin or insecticidally effective protoxin portion as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc. The concentration of the BTS02617A, BTS02618A, BTS02654B or BTS02652E strain, crystals, crystal proteins, or the BTS02618A protoxin, toxin or insecticidally effective protoxin portions in such a composition will depend upon the nature of the formulation and its intended mode of use. Generally, an insecticide composition of this invention can be used to protect a field for 2 to 4 weeks against Lepidoptera with each application of the composition. For more extended protection (e.g., for a whole growing season), additional amounts of the composition should be applied periodically.

A method for controlling insects, particularly Lepidoptera, in accordance with this invention preferably comprises applying (e.g., spraying), to a locus (area) to be protected, an insecticidal amount of the BTS02617A, BTS02618A, BTS02654B or BTS02652E strain, spores, crystals, crystal proteins or the BTS02168A protoxin, toxin or insecticidally effective protoxin portions, preferably the BTS2168A toxin. The locus to be protected can include, for example, the habitat of the insect pests or growing vegetation or an area where vegetation is to be grown.

To obtain the BTS02618A protoxin, cells of the BTS02617A, BTS02618A, BTS02654B or BTS02652E strain can be grown in a conventional manner on a suitable culture medium and then lysed using conventional means such as enzymatic degradation or detergents or the like. The protoxin can then be separated and purified by standard techniques such as chromatography, extraction, electrophoresis, or the like. The toxin can then be obtained by trypsin digestion of the protoxin.

The BTS02617A, BTS02618A, BTS02654B or BTS02652E cells can also be harvested and then applied intact, either alive or dead, preferably dried, to the locus to be protected. In this regard, it is preferred that a purified BTS02617A, BTS02618A, BTS02654B or BTS02652E strain (either alive or dead) be used, particularly a cell mass that is 90.0 to 99.9% of the BTS02617A, BTS02618A, BTS02654B or BTS02652E strain.

The BTS02617A, BTS02618A, BTS02654B, or BTS02652E cells, crystals or crystal proteins or the BTS02618 protoxin, toxin, or insecticidally effective protoxin portion can be formulated in an insecticidal composition in a variety of ways, using any number of conventional additives, wet or dry, depending upon the particular use. Additives can include wetting agents, detergents, stabilizers, adhering agents, spreading agents and extenders. Examples of such a composition include pastes, dusting powders, wettable powders, granules, baits and aerosol sprays. Other Bt cells, crystals, crystal proteins, protoxins, toxins, and insecticidally effective protoxin portions and other insecticides, as well as fungicides, biocides, herbicides and fertilizers, can be employed along with the BTS02617A, BTS02618A, BTS02654B or BTS02652E cells, crystals or crystal proteins or the BTS02618 protoxin, toxin or insecticidally effective protoxin portions to provide additional advantages or benefits. Such an insecticidal composition can be prepared in a conventional manner, and the amount of the BTS02617A, BTS02618A, BTS02654B or BTS02652E cells, crystals or crystal proteins or the BTS02618A protoxin, toxin or insecticidally effective protoxin portion employed depends upon a variety of factors, such as the insect pest targeted, the composition used, the type of area to which the composition is to be applied, and the prevailing weather conditions. Generally, the concentration of the BTS02618A protoxin, insecticidally effective protoxin portions or toxin will be at least about 0.1% by weight of the formulation to about 100% by weight of the formulation, more often from about 0.15% to about 0.8% by weight of the formulation.

In practice, some insects can be fed the BTS02618A protoxin, toxin, insecticidally effective protoxin portion or mixtures thereof in the protected area, that is in the area where such protoxin, toxin and/or insecticidally effective protoxin portion has been applied. Alternatively, some insects can be fed intact and alive cells of the BTS02617A, BTS02618A, BTS02654B or BTS02652E strain or transformants thereof, so that the insects ingest some of the strain's protoxin and suffer death or damage.

The following Examples illustrate the invention. The FIGURE and the sequence listing referred to in the Examples are as follows:

FIG. 1 Southern blot analysis of AluI-digested total DNA of Bt strain HD127 (lane 1), the BTS02618A strain (lane 2), Bt strain BTS02459 (containing cryIA(c), 81k, cryIC en cryIE, lane 3), and Bt strain BTS02480E (containing the same genes as HD-127, lane 4), using a mixture of DNA-probes for cryI crystal protein genes, including the cryIG probe (SEQ ID no. 1). Each band corresponds to a particular crystal protein gene. With these probes, the BTS02618A strain is found to contain the cryIA(b) gene and a novel gene, which is the bTS02618A gene, identified by an AluI fragment of approximately 530 bp, hybridizing to the cryIG probe of SEQ ID no. 1. The names of the recognized cryI genes are indicated, as well as the size of some fragments. The bTS02618A gene is indicated with three asterisks; "?" indicates an unknown gene fragment.

Sequence Listing

SEQ ID No. 1—Nucleotide sequence of the DNA probe used to isolate the bTS02618A gene. This probe is derived from part of the cryIG DNA sequence and is complementary to nucleotides 2732–2750 of the DNA sequence described by Smulevitch et al. (1991).

SEQ ID No. 2—The 5' partial nucleotide sequence of the bTS02618A gene, comprising the presumptive translation initiation codon at nucleotide position 195–197.

SEQ ID No. 3—The 3' partial nucleotide sequence of the bTS02618A gene (N: unknown nucleotide), comprising the presumptive translational stop codon at nucleotide position 1146–1148.

SEQ ID No. 4—The nucleotide sequence of the bTS02618A gene and the translated amino acid sequence of the BTS02618A protoxin. The open reading frame of the protoxin reaches from nucleotide 668 to nucleotide 4141. The translation initiation codon is at nucleotide position 668–670, the translation stop codon is at nucleotide position 4139–4141.

SEQ ID No. 5—The amino acid sequence corresponding to the coding region of the nucleotide sequence of SEQ ID No. 4.

Unless otherwise stated in the Examples, all procedures for making and manipulating recombinant DNA are carried out by the standardized procedures described in Sambrook et al., *Molecular Cloning—A Laboratory Manual*, Second Ed., Cold Spring Harbor Laboratory Press, New York (1989).

EXAMPLE 1

Characterization of the BTS02617A, BTS02618A, BTS02654B and BTS02652E Strains The BTS02617A, the BTS02618A and the BTS02654B strain were isolated from grain dust sampled in Cadlan, province of Bicol, The Philippines and were deposited at the BCCM-LMG on Jul. 2, 1992 under accession Nos. LMG P-12592, LMG P-12593 and LMG P-12594, respectively. Strain BTS02652E was also isolated from Philippine grain dust, and was deposited at the BCCM-LMG on Mar. 1, 1993 under accession No. LMG P-13493.

Each strain can be cultivated on conventional standard media, preferably $T_3$ medium (tryptone 3 g/l, tryptose 2 g/l, yeast extract 1.5 g/l, 5 mg $MnCl_2$, 0.05M $Na_2PO_4$, pH 6.8 and 1.5% agar), preferably at 28° C. For long term storage, it is preferred to mix an equal volume of a spore-crystal suspension with an equal volume of 50% glycerol and store this at −70° C. or lyophilize a spore-crystal suspension. For sporulation, growth on $T_3$ medium is preferred for 48 hours at 28° C., followed by storage at 4° C. During its vegetative phase, each of the strains can also grow under facultative anaerobic conditions, but sporulation only occurs under aerobic conditions.

Sterilization of each strain occurs by autoclave treatment at 120° C. (1 bar pressure) for 20 minutes. Such treatment totally inactivates the spores and the BTS02617A, BTS02618A, BTS02654B, and BTS02652E protoxins. UV radiation (254 nm) also inactivates the spores.

After cultivating on Nutrient Agar ("NA", Difco Laboratories, Detroit, Mich., U.S.A.) for one day, colonies of each of the BTS02617A, BTS02618A, BTS02654B and BTS02652E strains form opaque white colonies with irregular edges. Cells of each strain (Gram positive rods of 1.7–2.4×5.6–7.7 μm) sporulate after 48 hrs cultivation at 28° C. on $T_3$ agar. The crystal proteins produced during sporulation are packaged in crystals of the BTS02617A, BTS02618A, BTS02654B, and BTS02652E strains. Quite remarkably, the crystal remains attached to the spore after sporulation.

The Bt serotype of the BTS02617A, BTS02618A, BTS02645B and BTS02652E strains was determined to be serotype tolworthi H9 of all these strains which was determined by conventional serotyping methods as conducted by the WHO Collaborating Center for Entomopathogenic Bacillus.

EXAMPLE 2

Insecticidal Activity of the BTS02617A, BTS02618A, BTS02654B and BTS02652E Strains and the BTS02618A Protoxin against Noctuidae spp., Yponomeutidae spp. and Pyralidae spp.

Toxicity assays were performed on neonate larvae (for *Plutella xylostella*, third instar larvae were used) fed on an artificial diet layered with spore-crystal mixtures from one of the BTS02617A, BTS02618A, BTS02654B and BTS02652E strains or the BTS02618A protoxin or toxin. The artificial diet was dispensed in wells of Costar 24-well plates. Formaldehyde was omitted from the diet. 50 μl of a sample dilution was applied on the surface of the diet and dried in a laminar air flow. For $LC_{50}$ assays, the dilutions were made in a PBS-BSA buffer, and five dilutions were applied. Two larvae were placed in each well and 24 larvae were used per sample dilution. Dead and living *M. brassica, S. frugiperda, H. virescens, O. nubilalis, Plutella xylostella* and *S. exigua* larvae were counted on the fifth day, and dead and living *A. ipsilon* and *S. littoralis* larvae were counted on the sixth day. The $LC_{50}$ and $LC_{95}$ values (the concentrations required to kill respectively 50% or 95% of the insects tested, expressed in number of spore-crystals/cm$^2$ or ng (pro)toxin/cm$^2$) were calculated using Probit-analysis (Finney, 1971), and the results are set forth below.

*Spodoptera littoralis*

| Experiment/Strain | $LC_{50}$[a] | $LC_{95}$[a] | $FL_{min-max}$[b] | Slope |
|---|---|---|---|---|
| Experiment 1 | | | | |
| BTS02618A | 2.4 | 7.7 | 1.5–3.4 | 3.2 |
| HD127[c] | 2.5 | 168 | 1.2–7.4 | 1.0 |

-continued

| *Spodoptera littoralis* | | | | |
|---|---|---|---|---|
| Experiment/Strain | $LC_{50}$[a] | $LC_{95}$[a] | $FL_{min-max}$[b] | Slope |
| Experiment 2 | | | | |
| BTS02618A | 1.1 | 4 | 0.8–1.6 | 3.0 |
| HD127 | 21.2 | 133.7 | 14.4–31.9 | 2.0 |

[a]$10^5$ spore-crystals per $cm^2$
[b]95% fiducial limits of $LC_{50}$ values
[c]from the Howard Dulmage collection, housed at the Northern Region Research Center, 1815 North University, Peoria, Ill, USA. The curator is Dr. L. Nakamura.

Experiments with purified BTS02618A protoxin also show a significant toxicity of this protoxin against *S. littoralis* larvae.

| *Spodoptera exigua* | | | | |
|---|---|---|---|---|
| 1. Crystal/spore mixtures | | | | |
| Experiment/Strain | $LC_{50}$[a] | $LC_{95}$[a] | $FL_{min-max}$[b] | Slope |
| Experiment 1 | | | | |
| BTS02618A | 1.4 | 7.9 | 0.48–3.9 | 2.2 |
| HD127 | 8.2 | 163.5 | 5.1–15.7 | 1.3 |
| Experiment 2 | | | | |
| BTS02618A | 1.2 | 3.56 | 0.91–1.57 | 3.5 |
| BTS02617A | 0.79 | 2.12 | 0.61–1.03 | 3.81 |
| HD127 | 3.5 | 44.2 | 1.36–11.5* | 1.5 |
| Florbac | 4.1 | 53.9 | 1.5–17.0* | 1.47 |
| BTS00170U[c] | 5.1 | 46.5 | 1.83–24.4* | 1.71 |
| Experiment 3 | | | | |
| Javelin[d] | 23.12 | 195.7 | 14.6–56.7 | 1.77 |
| Experiment 4 | | | | |
| BTS02618A | 1.07 | 2.91 | 0.83–1.39 | 3.8 |
| BTS02617A | 0.87 | 4.7 | 0.59–1.21 | 2.22 |
| HD127 | 4.7 | 56.9 | 1.85–18.7* | 1.52 |
| Florbac[e] | 2.53 | 48.1 | 0.79–6.71* | 1.29 |
| BTS00170U | 1.94 | 56.3 | 0.55–5.4* | 1.12 |

[a]$10^5$ spore-crystals per $cm^2$
[b]95% fiducial limits of $LC_{50}$ values, values marked with * are 90% fiducial limits of $LC_{50}$ values
[c]PCT patent publication WO 90/06999
[d]strain isolated from Javelin ® (Sandoz, Lichtstrasse, Basel, Switzerland)
[e]strain from Florbac ® (Novo Nordisk, Novo Allè, Bagsværd, Denmark)

2.Toxin/protoxin assays.

| ICP | | $LC_{50}$[a] | $LC_{95}$[a] | $FL_{min-max}$[b] | Slope |
|---|---|---|---|---|---|
| BTS02618A | Protoxin | 26.6 | 100.6 | 20.9–33.9 | 2.8 |
| CryIC | Toxin | 68.9 | 313.2 | 50.5–94.1 | 2.5 |
| CryID | Toxin | 118.6 | 870.6 | 82.7–170.0 | 1.9 |

[a]ng/$cm^2$
[b]95% fiducial limits of $LC_{50}$ values

| *Mamestra brassica* | | | | |
|---|---|---|---|---|
| 1. Crystal/spore mixtures. | | | | |
| Experiment/Strain | $LC_{50}$[a] | $LC_{95}$[a] | $FL_{min-max}$[b] | Slope |
| HD127 | 37.8 | 297.6 | 17.8–91.1 | 1.8 |
| BTS02618A | 8.6 | 59.6 | 6.0–12.2 | 1.9 |
| BTS02617A | 5.2 | 25.8 | 3.7–7.1 | 2.4 |

-continued

| *Mamestra brassica* | | | | |
|---|---|---|---|---|
| BTS02652E | 12.9 | 44.2 | 9.7–17.2 | 3.0 |
| BTS02654B | 14.2 | 60.5 | 10.8–19.9 | 2.6 |

[a]$10^5$ spore-crystals per $cm^2$
[b]95% fiducial limits of $LC_{50}$ values

2. Protoxin assays.

| ICP | | $LC_{50}$[a] | $LC_{95}$[a] | $FL_{min-max}$[b] | Slope |
|---|---|---|---|---|---|
| BTS02618A | Protoxin | 25.3 | 125.1 | 19.3–33.2 | 2.4 |
| CryIC | Protoxin | 22.0 | 62.9 | 16.3–29.6 | 3.6 |
| CryIA(b) | Protoxin | 162.4 | 7169 | 93.2–283.1 | 1.0 |

[a]ng/$cm^2$
[b]95% fiducial limits of $LC_{50}$ values

| *Agrotis ipsilon* | | |
|---|---|---|
| 1.Crystal/spore mixtures. | | |
| Strain | mortality[a] | genes[b] |
| Btgall.[c] | 1/20 | cryIF, cryIG, cryII, 81k |
| HD127[d] | 2/20 | cryIAa, cryIAb, cryIC, cryID, cryII, 81k |
| BTS02618A | 16/20[e] | cryIAb, cryII, bTS02618A |
| Buffer | 1/20 | none |

[a]number of 1st instar larvae killed after 6 days ($10^7$ spore-crystals per $cm^2$)
[b]genes known to be present in these strains
[c]Btgall. as described by Smulevitch et al (1991)
[d]HD127 is available at the Howard Dulmage Collection (NRRC, see above)
[e]surviving larvae show severe growth-inhibition

| STRAIN | $LC_{50}$[a] | $LC_{95}$[b] | $FL_{min-max}$[b] | Slope |
|---|---|---|---|---|
| BTS02618A | 84.4 | 207.9 | 65.9–109.6 | 4.2 |
| HD127 | >250 | | | |
| BTS02617A | 53.4 | 261.0 | 27.7–112.3 | 2.4 |

[a]$10^6$ spores/$cm^2$
[b]95% fiducial limits of $LC_{50}$ values

2. Toxin/protoxin assay.

| ICP | | $LC_{50}$[a] | $LC_{95}$[a] | $FL_{min-max}$[b] | Slope |
|---|---|---|---|---|---|
| CryIAc | Toxin | >1350 | | | |
| BTS02618A | Protoxin | 212.2 | 1973 | 168.1–267.9 | 1.7 |

[a]ng/$cm^2$
[b]95% fiducial limits of $LC_{50}$ values

Since MacIntosh et al. (1990) described some activity of the CryIAc toxin towards *A. ipsilon*, purified CryIAc toxin was tested on this insect for comparison but did not cause any significant mortality of *A. ipsilon*.

| *Heliothis virescens* | | | | |
|---|---|---|---|---|
| 1.Crystal/spore mixture. | | | | |
| Experiment/Strain | $LC_{50}$[a] | $LC_{95}$[a] | $FL_{min-max}$[b] | Slope |
| BTS02617A | 1.69 | 14.99 | 0.67–2.89 | 1.73 |
| BTS02618A | 2.71 | 25.4 | 0.88–6.99 | 1.69 |
| BTS00170U[c] | 15.1 | 398.7 | 8.3–41.2 | 1.15 |
| Dipel[d] | 2.99 | 14.11 | 1.25–7.76 | 2.45 |

[a]$10^3$ spore-crystals per $cm^2$
[b]95% fiducial limits of $LC_{50}$ values
[c]PCT patent publication WO 90/06999
[d]strain isolated from Dipel ™ (Abbott Laboratories, North Chicago, Ill., USA)

-continued

| *Heliothis virescens* | | | | | |
|---|---|---|---|---|---|
| 2.Toxin/protoxin assay. | | | | | |
| ICP | | $LC_{50}$[a] | $FL_{min-max}$[b] | $LC_{95}$[a] | Slope |
| BTS02618A | Protoxin | 31.6 | 20–50 | 182.7 | 2.1 |
| CryIAb | Toxin | 7.2 | 4.9–10.5 | 169.1 | 1.2 |

[a]ng/cm$^2$
[b]95% fiducial limits of $LC_{50}$ values

| *Ostrinia nubilalis* | | | | |
|---|---|---|---|---|
| 1.Crystal/spore mixtures. | | | | |
| Experiment/Strain | $LC_{50}$[a] | $LC_{95}$[a] | $FL_{min-max}$[b] | Slope |
| BTS02617A | 4.92 | 12.49 | 2.45–6.81 | 4.0 |
| BTS02618A | 6.17 | 39.7 | 2.93–9.74 | 2.0 |
| Dipel[c] | >30 | | | |

[a]$10^5$ spore-crystals per cm$^2$
[b]95% fiducial limits of $LC_{50}$ values
[c]strain isolated from Dipel ™ (Abbott Laboratories)

2.Purified protoxin assay

| ICP | | 100% Mortality[a] |
|---|---|---|
| CryIAb | Toxin | 1350 |
| CryIB | Toxin | 1350 |
| BTS02618A | Protoxin | 100 |

[a]concentration at which 100% mortality was observed (in ng/cm$^2$)

The purified BTS02618A protoxin also showed a significant toxicity to *Ostrinia nubilalis* larvae, as compared with the CryI toxins that are most active against Ostrinia.

*Plutella xylostella*

*Plutella xylostella* larvae also showed significant mortality after application of purified BTS02618A toxin to their artificial diet in several experiments.

*Spodoptera frugiperda*

Crystal/spore mixtures of a bTS02618A gene-transformed crystal-minus Bt strain (Mahillon et al., 1989) were also found to significantly inhibit larval growth of *S. frugiperda* larvae in insect feeding trials.

In conclusion, the strains of this invention and the BTS02618A protein of this invention have a strong insecticidal activity against a broad range of insects that are not susceptible to any single currently available Bt protein and have an activity against at least three Spodoptera spp. and against other Noctuidae, such as *A. ipsilon, M. brassica* and *H. virescens,* as well as against Pyralidae, such as *O. nubilalis* and Yponomeutidae such as *Plutella xylostella*. These results are summarized and compared with results for other CryI genes (Van Frankenhuyzen, 1993) in Table 1 which shows the unique range of insects susceptible to the BTS02618A protein.

EXAMPLE 3

Identification of the bTS02618A Gene

The bTS02618A gene was identified in the BTS02618A strain by Southern blot analysis (FIG. 1) of AluI digested total DNA of the strain using, as a DNA probe, the DNA sequence of the cryIG gene (Gleave et al., 1992) of SEQ ID No. 1 and using standard hybridization conditions. Partial DNA sequences of the bTS02618A gene, showing its 5' and 3' end portions, are shown in SEQ ID Nos. 2 and 3, respectively, and the full DNA sequence of the bTS02618A gene and the full amino acid sequence of the BTS02618A protein are shown in SEQ ID No. 4.

The partial sequences of SEQ ID Nos. 2 and 3 allow the bTS02618A gene to be recognized in the BTS02617A, BTS02654B and BTS02652E strains and allow the construction of probes to identify and isolate the full gene sequence in these and other Bt strains. The translation initiation codon of the bTS02618A gene is identified at nucleotide position 195–197 in SEQ ID No. 2, corresponding to nucleotide position 668–670 in SEQ ID No.4. The translation stop codon is identified at nucleotide position 1146–1148 in SEQ ID No. 3, corresponding to nucleotide position 4139–4141 in SEQ ID No. 4.

The bTS02618A gene was also identified in the BTS02617A, BTS02654B and BTS02652E strains by using the DNA sequence of SEQ ID No. 1 as a probe, as well as other DNA probes of conserved DNA fragments in cryI genes.

The full length bTS02618A gene was found to encode a 129.9 kD protoxin. A comparison of the amino acid sequence with other known CryI proteins showed that the C-terminal part (C-terminal of conserved sequence block 5) was homologous with CryIG (88%). The best homology for the N-terminal part (the toxin) was found with the CryIB toxin, but this was found to be less than 50% (homology is expressed as the number of perfect matches divided by the number of amino acids of the longest fragment).

The smallest insecticidal protein is believed to be a 69 kD (615 amino acids) protein stretching from amino acid number 44 to amino acid number 658 in SEQ ID No. 4. A smaller tryptic fragment of 55 kD (494 amino acids), stretching from amino acid number 165 to amino acid number 658 in SEQ ID No. 4, still has insecticidal activity towards *S. exigua*, but this activity is significantly reduced. Thus, a truncated bTS02618A gene or an equivalent truncated gene preferably encodes the 69 kD protein of the BTS02618A protoxin of SEQ ID No. 4 as described above.

EXAMPLE 4

Cloning and Expression of the bTS02618A Gene

In order to isolate the bTS02618A gene, total DNA from the BTS02618A strain was prepared and partially digested with Sau3A. The digested DNA was size fractionated on a sucrose gradient and fragments ranging from 7 Kb to 10 Kb were ligated to the BamH1-digested and BAP-treated cloning vector pUC19 (Yannisch-Perron et al., 1985). Recombinant *E. coli* clones containing the vector were then screened with the cryIG DNA probe of SEQ ID No. 1 which is described in Example 3, to identify clones containing the bTS02618A gene.

The so-identified DNA fragments were then sequenced according to Maxam and Gilbert (1980). Partial sequences of the bTS02618A gene are shown in SEQ ID Nos. 2 and 3, and a full sequence of the bTS02618A gene and the BTS02618A protein is shown in SEQ ID No. 4. Based on the DNA sequence analysis, the gene is cut with appropriate restriction enzymes to give the truncated bTS02618A gene encoding the BTS02618A toxin. Expression of the gene in *E. coli* was induced using standard procedures (Sambrook et al., 1989, supra).

The bTS02618A gene is also introduced by routine procedures into a crystal-minus Bt strain, using Bt plasmids PGI2 or PGI3 (Mahillon and Seurinck 1988; Mahillon et al., 1988).

EXAMPLE 5

Insertion of the bTS02618A Gene and the Truncated bTS02618A Gene in *E. coli* and Insertion of the Truncated bTS02618A Gene in Plants In order to express the bTS02618A gene and the truncated bTS02618A gene of Example 4 in *E. coli* and in plants, different gene cassettes are made in *E. coli* according to the procedure described in EPA 86/300291.1 and EPA 88/402115.5.

To allow significant expression in plants, cassettes containing a) the truncated gene or b) a hybrid gene that is a fusion of i) the truncated gene and ii) the neo gene are each: inserted between the T-DNA border sequences of intermediate plant expression vectors as described in EPA 86/300291.1; fused to transcript formation and polyadenylation signals in the plant expression vectors; placed under the control of the constitutive promoter from cauliflower mosaic virus driving the 35S3 transcript (Hull and Howell, 1987) or the 2' promoter from the TR-DNA of the octopine Ti-plasmid (Velten et al., 1984); and fused to 3' end transcript formation and polyadenylation signals of the octopine synthase gene (Gielen et al., 1984).

Using standard procedures (Deblaere et al., 1985), the intermediate plant expression vectors, containing the truncated bTS02618A gene, are transferred into the Agrobacterium strain C58C1Rif$^R$ (U.S. patent application Ser. No. 821,582; EPA 86/300,291.1) carrying the disarmed Ti-plasmid pGV2260 (Vaeck et al., 1987). Selection for spectinomycin resistance yields cointegrated plasmids, consisting of pGV2260 and the respective intermediate plant expression vectors. Each of these recombinant Agrobacterium strains is then used to transform different cotton plants so that the truncated bTS02618A gene is contained in, and expressed by, different plant cells.

EXAMPLE 6

Expression of the Truncated bTS02618A Gene in Plants

The insecticidal activity against Lepidoptera of the expression products of the truncated bTS02618A gene in leaves of transformed plants, generated from the transformed plant cells of Example 5, is evaluated by recording the growth rate and mortality of Agrotis and Spodoptera spp. larvae fed on these leaves. These results are compared with the growth rate of larvae fed leaves from untransformed plants. Toxicity assays against Agrotis and Spodoptera spp. are performed as described in EP 0,358,557, U.S. patent application Ser. No. 821,582 and EPA 86/300,291.1. A significantly higher mortality rate is obtained among larvae fed on leaves of transformed plants containing the truncated bTS02618A gene and the truncated bTS02618A-neo hybrid gene than among larvae fed the leaves of untransformed plants. The transformed plants are also found to resist *Ostrinia nubilalis Mamestra brassica, Heliothis virescens* and *Plutella xylostella* attack by their expression of the BTS02618A protein.

Needless to say, this invention is not limited to the BTS02617A strain (BCCM-LMG P-12592), the BTS02618A strain (BCCM-LMG P-12593), the BTS02654B strain (BCCM-LMG P-12594) and the BTS02652E (BCCM-LMG P-13493) strain. Rather, the invention also includes any mutant or variant of the BTS02617A, BTS02618A, BTS02654B, and BTS02652E strain which produces crystals, crystal proteins, protoxin or toxin having substantially the same properties, particularly anti-Lepidoptera properties, quite particularly anti-Noctuidae, anti-Yponomeutidae and anti-Pyralidae properties, especially anti-Spodoptera, anti-Plutella, anti-Ostrinia anti-Mamestra; anti-Heliothis and anti-Agrotis properties, as the respective BTS02617A, BTS02618A, BTS02654B or BTS02652E crystals or crystal proteins, or the BTS02618A protoxin or toxin. This invention also includes the bTS02618A gene and any insecticidally effective parts thereof, like the truncated bTS02618A gene. In this regard, the term "bTS02618A gene" as used herein means the gene isolated from the BTS02617A, BTS02618A, BTS02654B or BTS02652E strain and hybridizing to the nucleotide sequence of SEQ ID No. 1 and any equivalent gene encoding a protoxin having substantially the same amino acid sequence and insecticidal activity as the BTS02618A protoxin and preferably containing the partial nucleotide sequences shown in SEQ ID Nos. 2 and 3, or the full sequence shown in SEQ ID No. 4.

This invention also is not limited to cotton plants transformed with the truncated bTS02618A gene. It includes any plant, such as tomato, tobacco, rapeseed, alfalfa, sunflower, lettuce, potato, corn, rice, soybean, Brassica species, sugar beet and other legumes and vegetables, transformed with an insecticidally effective part of the bTS02618A gene or an equivalent gene.

Nor is this invention limited to the use of *Agrobacterium tumefaciens* Ti-plasmids for transforming plant cells with an insecticidally effective bTS02618A gene part. Other known techniques for plant cell transformations, such as by means of liposomes, by electroporation or by vector systems based on plant viruses or pollen, can be used for transforming monocotyledons and dicotyledons with such a gene part.

Furthermore, DNA sequences other than those present naturally in the BTS02617A, BTS02618A, BTS02654B and BTS02652E strains and encoding the BTS02618A protoxin and toxin can be used for transforming plants and bacteria. In this regard, the natural DNA sequence of these genes can be modified by: 1) replacing some codons with others that code either for the same or different, preferably the same, amino acids; 2) deleting or adding some codons; and/or 3) reciprocal recombination as described by Ge et al. (1991); provided that such modifications do not substantially alter the properties, particularly the insecticidal properties, especially anti-lepidoptera properties, of the encoded, insecticidally effective portions of the BTS02618A protoxin (e.g., toxin). For example, an artificial bTS02618A gene or gene part of this invention, as described above, having a modified codon usage, could be used in certain circumstances instead of a natural insecticidally effective bTS02618A gene part in a bTS02618A chimeric gene of this invention for transforming plants.

Also, other DNA recombinants containing all or part of the bTS02618A gene in association with other foreign DNA, particularly the DNA of vectors suitable for transforming plants and microorganisms other than *E. coli*, are encompassed by this invention. In this regard, this invention is not limited to the specific plasmids containing the bTS02618A gene, or parts thereof, that were heretofore described, but rather, this invention encompasses any DNA recombinants containing DNA sequences that are their equivalent. Further, the invention relates to all DNA recombinants that include all or part of the bTS02618A gene and that are suitable for transforming microorganisms (e.g., plant associated bacteria such as other *Bacillus thuringiensis* strains, *Bacillus subtilis*, Pseudomonas, and Xanthomonas or yeasts such as *Strepto-*

*myces cerevisiae*) under conditions which enable all or part of the gene to be expressed and to be recoverable from said microorganisms or to be transferred to a plant cell.

TABLE 1

Activity of CryI proteins towards several lepidopteran insect pests: + and − indicates the presence or absence of insecticidal activity, +/− indicates low activity (according to Van Frankenhuyzen (1993)), NA indicates no data available, the protein BTS02618A is abbreviated as 2618A (data of Van Frankenhuyzen (1993) and this invention (for *A. ipsilon* and 2618A))

| | 2618A | IAb | IAc | IB | IC | IF |
|---|---|---|---|---|---|---|
| *S.exigua* | + | +/− | − | − | + | + |
| *S.littoralis* | + | − | − | − | + | NA |
| *H.virescens* | + | + | + | − | +/− | + |
| *A.ipsilon* | + | NA | − | NA | NA | NA |
| *O.nubilalis* | + | + | + | NA | NA | + |
| *P.xylostella* | + | + | + | + | + | NA |
| *M.brassica* | + | + | − | − | + | NA |

REFERENCES

Berhard, K. and Utz, R., "Production of *Bacillus thuringiensis* insecticides for experimental and commercial uses", In *Bacillus thuringiensis*, An Environmental Biopesticide: Theory and Practice, pp.255–267, eds. Entwistle, P. F., Cory, J. S., Bailey, M. J. and Higgs, S., John Wiley and Sons, New York (1993).

Chassy, *B. M., Mercenier, A. and Flickinger, J., Trends Biotechnol.* 6, 303–309 (1988).

Datta S., Peterhans A., Datta K. and Potrykus I., Bio/Technology 8, 736–740 (1990).

Deblaere, R., Bijtebier, B. De Greve, H., Debock, F., Schell, J., Van Montagu, M. and Leemans, J., Nucleic Acids Research 13, 4777–4788 (1985).

Dulmage, H. T., "Production of Bacteria for Biological Control of Insects" in *Biological Control in Crop Production*, Ed. Paparizas, D. C., Osmun Publishers, Totowa, N.J., U.S.A., pp. 129–141 (1981).

Finney, Probit Analysis, 3rd Edition, Cambridge University Press (1971)

Franck, Guilley, Jonard, Richards and Hirth, Cell 21, 285–294 (1980)

French, B. T., Maul, H. N. and Maul, G. G., Anal. Biochem. 156, 417–423 (1986)

Fromm M., Morrish F., Armstrong C., Williams R., Thomas J. and Klein T., Bio/Technology 8, 833–839 (1990).

Gardner, Howarth, Hahn, Brown-Luedi, Shepard and Messing, Nucleic Acids Research 9, 2871–2887 (1981)

Ge A., Rivers D., Milne R. and Dean D., J. Biol. Chem. 266, 17954–17958 (1991)

Gielen, J., De Beukeleer, M., Seurinck, J., Deboeck, F., De Greve, H., Lemmers, M., Van Montagu, M. and Schell, J., EMBO J 3, 835–845 (1984).

Gleave, A. P., Hegdes, R. J. and Broadwell, A. H., J. Gen. Microbiol. 138, 55–62 (1992).

Gordon-Kamm W., Spencer M., Mangano M., Adams T., Daines R., Start W., O'Brien J., Chambers S., Adams W., Willets N., Rice T., Mackey C., Krueger R., Kausch A. and Lemaux P., The Plant Cell 2, 603–618 (1990).

Gould, J., Devey, M., Hasegawa, O., Ulian, E. C., Peterson, G. and Smith, R. H., Plant Physiol. 95, 426–434 (1991).

Höfte, H., De Greve, H., Seurinck, J., Jansens, S., Mahillon, J., Ampe, Vandekerckhove, J, Vanderbruggen, H., Van Montagu, M., Zabeau, M. and Vaeck, M., Eur. J. Biochem. 161, 273–280 (1986)

Höfte, H., Van Rie, J., Jansens, S., Van Houtven, A., Verbruggen, H. and Vaeck, M., Applied and Environmental Microbiology 54, 2010–2017 (1988)

Höfte H. and Whiteley H. R., Microbiological Review 53, 242–255 (1989).

Hull and Howell, Virology 86, 482–493 (1987)

Lereclus, D.; Vallade, M.; Chaufaux, J.; Arantes, O. & Rambaud, S., Bio/Technology 10, 418 (1992).

MacIntosh, S. C. et al, J. Invertebrate Patholog. 56, 258–266 (1990).

Mahillon, J. and Delcour, J., J. Microbiol. Methods 3, 69–73 (1984).

Mahillon, J. and Seurinck, J., Nucl. Acids Res. 16, 11827–11828 (1988).

Mahillon et al, Plasmid 19, 169–173 (1988).

Mahillon et al, FEMS Microbiol. Letters 60, 205–210 (1989).

Maxam, A. M. and Gilbert, W., Methods in Enzymol. 65, 499–560 (1980).

Murray, E., Lotzer, J. and Eberle, M., Nucleic Acids Research 17(2), 477–498 (1989).

Shimamoto K., Terada R., Izawa T. and Fujimoto H., Nature 338, 274–276 (1989).

Smulevitch, S. V., Osterman, A. L., Shevelev, A. B. , Kaluger, S. V., Karasin, A. I., Kadyrov, R. M., Zagnitko, O. P., Chestukhina, G. G. and Stepanov, V. M., FEBS Lett. 293, 1(2), 25–28 (1991).

Stanssens P., Opsomer C., McKeown Y., Kramer W., Zabeau M. and Fritz H. J., Nucleic Acids Research 12, 4441–4454 (1989).

Vaeck, M., Reynaerts, A., Höfte, H., Jansens, S., De Beuckeleer, M., Dean, C., Zabeau, M., Van Montagu, M. and Leemans, J., Nature 327, 33–37(1987).

Van Frankenhuyzen, "The Challenge of *Bacillus thuringiensis*", in "*Bacillus thurinpiensis*, An Environmental Biopesticide: Theory and Practice", pp.1–35, eds. Entwistle, P. F., Cory, J. S., Bailey, M. J. and Higgs, S., John Wiley and Sons, New York (1993).

Velten, J., Velten, L., Hain, R. and Schell, J., EMBO J 3, 2723–2730 (1984).

Velten, J. and Schell, J. Nucleic Acids Research 13, 6981–6998 (1985)

Visser, B., Bosch, D. and Honée, G., "Domain-Structure Studies of *Bacillus thuringiensis* Crystal Proteins: A Genetic Approach", In *Bacillus thuringiensis*, An Environmental Biopesticide: Theory and Practice, pp.71–88, eds. Entwistle, P. F., Cory, J. S., Bailey, M. J. and Higgs, S., John Wiley and Sons, New York (1993).

Yannisch-Perron, C., Vierra, J. and Messing, J., Gene 33, 103–119 (1985).

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( i x ) FEATURE:
( A ) NAME/KEY: misc_feature
( B ) LOCATION:1..19
( D ) OTHER INFORMATION:/function="for isolating bTS02618A gene from its containing strain"
/ note= "the probe is a part of the coding DNA strand of the cryIG gene (Smulevitch et al. (1991)"

( i x ) FEATURE:
( A ) NAME/KEY: misc_feature
( B ) LOCATION:1..19
( D ) OTHER INFORMATION:/note= "this probe is used to isolate the bTS02618A gene from its containing strain"

( x i ) SEQUENCE DESCRIPTION: SEQ ID NO: 1:

TTCTGTACTA TTGATTGTA 19

( 2 ) INFORMATION FOR SEQ ID NO: 2:

( i ) SEQUENCE CHARACTERISTICS:
( A ) LENGTH: 1561 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: BTS02618A ( i x ) FEATURE:
( A ) NAME/KEY: misc_feature
( B ) LOCATION:1..1561
( D ) OTHER INFORMATION:/note= "contains the translation initiation codon of the bTS02618A gene"

( x i ) SEQUENCE DESCRIPTION: SEQ ID NO: 2:

AAAAAGAAAT AGGAATAAAT ACTATCCATT TTTTCAAGAA ATATTTTTTT ATTAGAAAGG 60

AATCTTTCTT ACACGGGAAA ATCCTAAGAT TGAGAGTAAA GATATATATA TATAAATACA 120

ATAAAGAGTT TGTCAGGATT TTTGAAAGAT ATGATATGAA CATGCACTAG ATTTATAGTA 180

TAGGAGGAAA AAGTATGAAT CGAAATAATC AAAATGAATA TGAAATTATT GATGCCCCCC 240

ATTGTGGGTG TCCATCAGAT GACGATGTGA GGTATCCTTT GGCAAGTGAC CCAAATGCAG 300

CGTTACAAAA TATGAACTAT AAAGATTACT TACAAATGAC AGATGAGGAC TACACTGATT 360

CTTATATAAA TCCTAGTTTA TCTATTAGTG GTAGAGATGC AGTTCAGACT GCGCTTACTG 420

TTGTTGGGAG AATACTCGGG GCTTTAGGTG TTCCGTTTTC TGGACAAATA GTGAGTTTTT 480

-continued

```
ATCAATTCCT TTTAAATACA CTGTGGCCAG TTAATGATAC AGCTATATGG GAAGCTTTCA    540
TGCGACAGGT GGAGGAACTT GTCAATCAAC AAATAACAGA ATTTGCAAGA AATCAGGCAC    600
TTGCAAGATT GCAAGGATTA GGAGACTCTT TTAATGTATA TCAACGTTCC CTTCAAAATT    660
GGTTGGCTGA TCGAAATGAT ACACGAAATT TAAGTGTTGT TCGTGCTNAA TTTATAGCTT    720
TAGACCTTGA TTTTGTTAAT GCTATTCCAT TGTTTGCAGT AAATGGACAG CAGGTTCCAT    780
TACTGTCAGT ATATGCACAA GCTGTGAATT TACATTTGTT ATTATTAAAA GATGCATCTC    840
TTTTTGGAGA AGGATGGGGA TTCACACAGG GGGAAATTTC CACATATTAT GACCGTCAAT    900
TGGAACTAAC CGCTAAGTAC ACTAATTACT GTGAAACTTG GTATAATACA GGTTTAGATC    960
GTTTAAGAGG AACAAATACT GAAAGTTGGT TAAGATATCA TCAATTCCGT AGAGAAATGA   1020
CTTTAGTGGT ATTAGATGTT GTGGCGCTAT TTCCATATTA TGATGTACGA CTTTATCCAA   1080
CGGGATCAAA CCCACAGCTT ACACGTGAGG TATATACAGA TCCGATTGTA TTTAATCCAC   1140
CAGCTAATGT TGGACTTTGC CGACGTTGGG GTACTAATCC CTATAATACT TTTTCTGAGC   1200
TCGAAAATGC CTTCATTCGC CCACCACATC TTTTTGATAG GCTGAATAGC TTAACAATCA   1260
GCAGTAATCG ATTTCCAGTT TCATCTAATT TTATGGATTA TTGGTCAGGA CATACGTTAC   1320
GCCGTAGTTA TCTGAACGAT TCAGCAGTAC AAGAAGATAG TTATGGCCTA ATTACAACCA   1380
CAAGAGCAAC AATTAATCCC GGAGTTGATG GAACAAACCG CATAGAGTCA ACGGCAGTAG   1440
ATTTTCGTTC TGCATTGATA GGTATATATG GCGTGAATAG AGCTTCTTTT GTCCCAGGAG   1500
GCTTGTTTAA TGGTACGACT TCTCCTGCTA ATGGAGGATG TAGAGATCTC TATGATACAA   1560
A                                                                    1561
```

( 2 ) INFORMATION FOR SEQ ID NO: 3:

( i ) SEQUENCE CHARACTERISTICS:
( A ) LENGTH: 1554 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: BTS02618A ( i x ) FEATURE:
( A ) NAME/KEY: misc_feature
( B ) LOCATION:1146..1148
( D ) OTHER INFORMATION:/note= "Presumed translational stop codon of bTS02618A gene"

( x i ) SEQUENCE DESCRIPTION: SEQ ID NO: 3:

```
AAAATTATCC AACATACATT TATCAAAAAG TAGATGCATC GGTGTTAAAG CCTTATACAC     60
GCTATAGACT AGATGGATTT GTGAAGAGTA GTCAAGATTT AGAAATTGAT CTCATCCACC    120
ATCATAAAGT CCATCTTGTA AAAAATGTAC CAGATAATTT AGTATCTGAT ACTTACTCAG    180
ATGGTTCTTG CAGCGGAATC AACCGTTGTG ATGAACAGCA TCAGGTAGAT ATGCAGCTAG    240
ATGCGGAGCA TCATCCAATG GATTGCTGTG AAGCGGCTCA AACACATGAG TTTTCTTCCT    300
ATATTAATAC AGGGGATCTA AATGCAAGTG TAGATCAGGG CATTTGGGTT GTATTAAAAG    360
TTCGAACAAC AGATGGGTAT GCGACGTTAG GAAATCTTGA ATTGGTAGAG GTTGGGCCAT    420
TATCGGGTGA ATCTCTAGAA CGGGAACAAA GAGATAATGC GAAATGGAAT GCAGAGCTAG    480
```

-continued

GAAGAAAACG TGCAGAAATA GATCGTGTGT ATTTAGCTGC GAAACAAGCA ATTAATCATC 540

TGTTTGTAGA CTATCAAGAT CAACAATTAA ATCCAGAAAT TGGGCTAGCA GAAATTAATG 600

AAGCTTCAAA TCTTGTAGAG TCAATTTCGG GTGTATATAG TGATACACTA TTACAGATTC 660

CTGGGATTAA CTACGAAATT TACACAGAGT TATCCGATCG CTTACAACAA GCATCGTATC 720

TGTATACGTC TAGAAATGCG GTGCAAAATG GAGACTTTAA CAGTGGTCTA GATAGTTGGA 780

ATACAACTAT GGATGCATCG GTTCAGCAAG ATGGCAATAT GCATTTCTTA GTTCTTTCGC 840

ATTGGGATGC ACAAGTTTCC CAACAATTGA GAGTAAATCC GAATTGTAAG TATGTCTTAC 900

GTGTGACAGC AAGAAAAGTA GGAGGCGGAG ATGGATACGT CACAATCCGA GATGGCGCTC 960

ATCACCAAGA AACTCTTACA TTTAATGCAT GTGACTACGA TGTAAATGGT ACGTATGTCA 1020

ATGACAATTC GTATATAACA GAAGAAGTGG TATTCTACCC AGAGACAAAA CATATGTGGG 1080

TAGAGGTGAG TGAATCCGAA GGTTCATTCT ATATAGACAG TATTGAGTTT ATTGAAACAC 1140

AAGAGTAGAA GAGGGGGATC CTAACGTATA GCAACTATGA GAGGATACTC CGTACAAACA 1200

AAGATTAAAA AAAGGTAAAA TGAATAGAAC CCCCTACTGG TAGAAGGACC GATAGGGGGT 1260

TCTTACATGA AAAAATGTAG CTGTTTACTA AGGTGTATAA AAAACAGCAT ATCTGATAGA 1320

AAAAAGTGAG TACCTTATAA AGAAAGAATT CCATTCACAG TTTCGGTATC ATATAAATAA 1380

TGATAGGGGT ATCCTTCTTA TTTACATTAT TTTTCGCAAT TATCTCGACG TTCTTCTTTC 1440

CGCTCACAAT GATGATGATC ATGACAACAA TCGCGTCCAT AGCGAACTCT TTCGATATTA 1500

ATAATATCTA AACTCGTGTA GCAGTCATTT CCATTTTTTT TGATCCAGTA AATA 1554

( 2 ) INFORMATION FOR SEQ ID NO: 4:

( i ) SEQUENCE CHARACTERISTICS:
( A ) LENGTH: 4344 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION:668..4141

( i x ) FEATURE:
( A ) NAME/KEY: misc_feature
( B ) LOCATION:1..4344
( D ) OTHER INFORMATION:/note= "encompasses entire sequence of SEQ ID NO (SID) 2: from nt position 474 to 2034 in SID 4"

( i x ) FEATURE:
( A ) NAME/KEY: misc_feature
( B ) LOCATION:1..4344
( D ) OTHER INFORMATION:/note= "also encompasses part of the sequence of SID 3: from nt position 2994 to 4344 in SID 4"

( i x ) FEATURE:
( A ) NAME/KEY: misc_feature
( B ) LOCATION:1..4344
( D ) OTHER INFORMATION:/note= "SID 3 shows additional nucleotides, located 3'from the sequence shown in SID 4 ( 1352-1554 in SID 4 )"

( x i ) SEQUENCE DESCRIPTION: SEQ ID NO: 4:

GAATTCGAGC TCGGTACCTT TTCAGTGTAT CGTTTCCCTT CCATCAGGTT TTCAAATTGA 60

AAAGCCGAAT GATTTGAAAC TTGTTTACGA TGTAAGTCAT TTGTCTATGA CGAAAGATAC 120

GTGTAAAAAA CGTATTGAGA TTGATGAATG TGGACAAGTA GAAATTGACT TACAAGTATT 180

-continued

```
AAAGATTAAG GGTGTCCTTT CTTTTATCGG AAATTTCTCT ATTGAACCTA TTCTGTGTGA     240

AAACATGTAT ACAACGGTTG ATAGAGATCC GTCTATTTCC TTAAGTTTCC AAGATACGGT     300

ATATGTGGAC CATATTTTAA AATATAGCGT CCAACAACTA CCATATTATG TAATTGATGG     360

TGATCATATT CAAGTACGTG ATTTACAAAT CAAACTGATG AAAGAGAATC CGCAATCTGC     420

TCAAGTATCA GGTTTGTTTT GTTTTGTATA TGAGTAAGAA CCGAAGGTTT GTAAAAAAGA     480

AATAGGAATA AATACTATCC ATTTTTTCAA GAAATATTTT TTTATTAGAA AGGAATCTTT     540

CTTACACGGG AAAATCCTAA GATTGAGAGT AAAGATATAT ATATATAAAT ACAATAAAGA     600

GTTTGTCAGG ATTTTTGAAA GATATGATAT GAACATGCAC TAGATTTATA GTATAGGAGG     660

AAAAAGT ATG AAT CGA AAT AAT CAA AAT GAA TAT GAA ATT ATT GAT GCC       709
        Met Asn Arg Asn Asn Gln Asn Glu Tyr Glu Ile Ile Asp Ala
          1               5                  10

CCC CAT TGT GGG TGT CCA TCA GAT GAC GAT GTG AGG TAT CCT TTG GCA       757
Pro His Cys Gly Cys Pro Ser Asp Asp Asp Val Arg Tyr Pro Leu Ala
 15                  20                  25                  30

AGT GAC CCA AAT GCA GCG TTA CAA AAT ATG AAC TAT AAA GAT TAC TTA       805
Ser Asp Pro Asn Ala Ala Leu Gln Asn Met Asn Tyr Lys Asp Tyr Leu
                 35                  40                  45

CAA ATG ACA GAT GAG GAC TAC ACT GAT TCT TAT ATA AAT CCT AGT TTA       853
Gln Met Thr Asp Glu Asp Tyr Thr Asp Ser Tyr Ile Asn Pro Ser Leu
             50                  55                  60

TCT ATT AGT GGT AGA GAT GCA GTT CAG ACT GCG CTT ACT GTT GTT GGG       901
Ser Ile Ser Gly Arg Asp Ala Val Gln Thr Ala Leu Thr Val Val Gly
         65                  70                  75

AGA ATA CTC GGG GCT TTA GGT GTT CCG TTT TCT GGA CAA ATA GTG AGT       949
Arg Ile Leu Gly Ala Leu Gly Val Pro Phe Ser Gly Gln Ile Val Ser
     80                  85                  90

TTT TAT CAA TTC CTT TTA AAT ACA CTG TGG CCA GTT AAT GAT ACA GCT       997
Phe Tyr Gln Phe Leu Leu Asn Thr Leu Trp Pro Val Asn Asp Thr Ala
 95                 100                 105                 110

ATA TGG GAA GCT TTC ATG CGA CAG GTG GAG GAA CTT GTC AAT CAA CAA      1045
Ile Trp Glu Ala Phe Met Arg Gln Val Glu Glu Leu Val Asn Gln Gln
                115                 120                 125

ATA ACA GAA TTT GCA AGA AAT CAG GCA CTT GCA AGA TTG CAA GGA TTA      1093
Ile Thr Glu Phe Ala Arg Asn Gln Ala Leu Ala Arg Leu Gln Gly Leu
            130                 135                 140

GGA GAC TCT TTT AAT GTA TAT CAA CGT TCC CTT CAA AAT TGG TTG GCT      1141
Gly Asp Ser Phe Asn Val Tyr Gln Arg Ser Leu Gln Asn Trp Leu Ala
        145                 150                 155

GAT CGA AAT GAT ACA CGA AAT TTA AGT GTT GTT CGT GCT CAA TTT ATA      1189
Asp Arg Asn Asp Thr Arg Asn Leu Ser Val Val Arg Ala Gln Phe Ile
    160                 165                 170

GCT TTA GAC CTT GAT TTT GTT AAT GCT ATT CCA TTG TTT GCA GTA AAT      1237
Ala Leu Asp Leu Asp Phe Val Asn Ala Ile Pro Leu Phe Ala Val Asn
175                 180                 185                 190

GGA CAG CAG GTT CCA TTA CTG TCA GTA TAT GCA CAA GCT GTG AAT TTA      1285
Gly Gln Gln Val Pro Leu Leu Ser Val Tyr Ala Gln Ala Val Asn Leu
                195                 200                 205

CAT TTG TTA TTA TTA AAA GAT GCA TCT CTT TTT GGA GAA GGA TGG GGA      1333
His Leu Leu Leu Leu Lys Asp Ala Ser Leu Phe Gly Glu Gly Trp Gly
            210                 215                 220

TTC ACA CAG GGG GAA ATT TCC ACA TAT TAT GAC CGT CAA TTG GAA CTA      1381
Phe Thr Gln Gly Glu Ile Ser Thr Tyr Tyr Asp Arg Gln Leu Glu Leu
        225                 230                 235

ACC GCT AAG TAC ACT AAT TAC TGT GAA ACT TGG TAT AAT ACA GGT TTA      1429
Thr Ala Lys Tyr Thr Asn Tyr Cys Glu Thr Trp Tyr Asn Thr Gly Leu
    240                 245                 250
```

-continued

```
GAT CGT TTA AGA GGA ACA AAT ACT GAA AGT TGG TTA AGA TAT CAT CAA     1477
Asp Arg Leu Arg Gly Thr Asn Thr Glu Ser Trp Leu Arg Tyr His Gln
255                 260                 265                 270

TTC CGT AGA GAA ATG ACT TTA GTG GTA TTA GAT GTT GTG GCG CTA TTT     1525
Phe Arg Arg Glu Met Thr Leu Val Val Leu Asp Val Val Ala Leu Phe
                275                 280                 285

CCA TAT TAT GAT GTA CGA CTT TAT CCA ACG GGA TCA AAC CCA CAG CTT     1573
Pro Tyr Tyr Asp Val Arg Leu Tyr Pro Thr Gly Ser Asn Pro Gln Leu
            290                 295                 300

ACA CGT GAG GTA TAT ACA GAT CCG ATT GTA TTT AAT CCA CCA GCT AAT     1621
Thr Arg Glu Val Tyr Thr Asp Pro Ile Val Phe Asn Pro Pro Ala Asn
        305                 310                 315

GTT GGA CTT TGC CGA CGT TGG GGT ACT AAT CCC TAT AAT ACT TTT TCT     1669
Val Gly Leu Cys Arg Arg Trp Gly Thr Asn Pro Tyr Asn Thr Phe Ser
    320                 325                 330

GAG CTC GAA AAT GCC TTC ATT CGC CCA CCA CAT CTT TTT GAT AGG CTG     1717
Glu Leu Glu Asn Ala Phe Ile Arg Pro Pro His Leu Phe Asp Arg Leu
335                 340                 345                 350

AAT AGC TTA ACA ATC AGC AGT AAT CGA TTT CCA GTT TCA TCT AAT TTT     1765
Asn Ser Leu Thr Ile Ser Ser Asn Arg Phe Pro Val Ser Ser Asn Phe
                355                 360                 365

ATG GAT TAT TGG TCA GGA CAT ACG TTA CGC CGT AGT TAT CTG AAC GAT     1813
Met Asp Tyr Trp Ser Gly His Thr Leu Arg Arg Ser Tyr Leu Asn Asp
            370                 375                 380

TCA GCA GTA CAA GAA GAT AGT TAT GGC CTA ATT ACA ACC ACA AGA GCA     1861
Ser Ala Val Gln Glu Asp Ser Tyr Gly Leu Ile Thr Thr Thr Arg Ala
        385                 390                 395

ACA ATT AAT CCC GGA GTT GAT GGA ACA AAC CGC ATA GAG TCA ACG GCA     1909
Thr Ile Asn Pro Gly Val Asp Gly Thr Asn Arg Ile Glu Ser Thr Ala
    400                 405                 410

GTA GAT TTT CGT TCT GCA TTG ATA GGT ATA TAT GGC GTG AAT AGA GCT     1957
Val Asp Phe Arg Ser Ala Leu Ile Gly Ile Tyr Gly Val Asn Arg Ala
415                 420                 425                 430

TCT TTT GTC CCA GGA GGC TTG TTT AAT GGT ACG ACT TCT CCT GCT AAT     2005
Ser Phe Val Pro Gly Gly Leu Phe Asn Gly Thr Thr Ser Pro Ala Asn
                435                 440                 445

GGA GGA TGT AGA GAT CTC TAT GAT ACA AAT GAT GAA TTA CCA CCA GAT     2053
Gly Gly Cys Arg Asp Leu Tyr Asp Thr Asn Asp Glu Leu Pro Pro Asp
            450                 455                 460

GAA AGT ACC GGA AGT TCA ACC CAT AGA CTA TCT CAT GTT ACC TTT TTT     2101
Glu Ser Thr Gly Ser Ser Thr His Arg Leu Ser His Val Thr Phe Phe
        465                 470                 475

AGC TTT CAA ACT AAT CAG GCT GGA TCT ATA GCT AAT GCA GGA AGT GTA     2149
Ser Phe Gln Thr Asn Gln Ala Gly Ser Ile Ala Asn Ala Gly Ser Val
    480                 485                 490

CCT ACT TAT GTT TGG ACC CGT CGT GAT GTG GAC CTT AAT AAT ACG ATT     2197
Pro Thr Tyr Val Trp Thr Arg Arg Asp Val Asp Leu Asn Asn Thr Ile
495                 500                 505                 510

ACC CCA AAT AGA ATT ACA CAA TTA CCA TTG GTA AAG GCA TCT GCA CCT     2245
Thr Pro Asn Arg Ile Thr Gln Leu Pro Leu Val Lys Ala Ser Ala Pro
                515                 520                 525

GTT TCG GGT ACT ACG GTC TTA AAA GGT CCA GGA TTT ACA GGA GGG GGT     2293
Val Ser Gly Thr Thr Val Leu Lys Gly Pro Gly Phe Thr Gly Gly Gly
            530                 535                 540

ATA CTC CGA AGA ACA ACT AAT GGC ACA TTT GGA ACG TTA AGA GTA ACG     2341
Ile Leu Arg Arg Thr Thr Asn Gly Thr Phe Gly Thr Leu Arg Val Thr
        545                 550                 555

GTT AAT TCA CCA TTA ACA CAA CAA TAT CGC CTA AGA GTT CGT TTT GCC     2389
Val Asn Ser Pro Leu Thr Gln Gln Tyr Arg Leu Arg Val Arg Phe Ala
    560                 565                 570
```

-continued

```
TCA ACA GGA AAT TTC AGT ATA AGG GTA CTC CGT GGA GGG GTT TCT ATC   2437
Ser Thr Gly Asn Phe Ser Ile Arg Val Leu Arg Gly Gly Val Ser Ile
575                 580                 585                 590

GGT GAT GTT AGA TTA GGG AGC ACA ATG AAC AGA GGG CAG GAA CTA ACT   2485
Gly Asp Val Arg Leu Gly Ser Thr Met Asn Arg Gly Gln Glu Leu Thr
                595                 600                 605

TAC GAA TCC TTT TTC ACA AGA GAG TTT ACT ACT ACT GGT CCG TTC AAT   2533
Tyr Glu Ser Phe Phe Thr Arg Glu Phe Thr Thr Thr Gly Pro Phe Asn
            610                 615                 620

CCG CCT TTT ACA TTT ACA CAA GCT CAA GAG ATT CTA ACA GTG AAT GCA   2581
Pro Pro Phe Thr Phe Thr Gln Ala Gln Glu Ile Leu Thr Val Asn Ala
        625                 630                 635

GAA GGT GTT AGC ACC GGT GGT GAA TAT TAT ATA GAT AGA ATT GAA ATT   2629
Glu Gly Val Ser Thr Gly Gly Glu Tyr Tyr Ile Asp Arg Ile Glu Ile
    640                 645                 650

GTC CCT GTG AAT CCG GCA CGA GAA GCG GAA GAG GAT TTA GAA GCG GCG   2677
Val Pro Val Asn Pro Ala Arg Glu Ala Glu Glu Asp Leu Glu Ala Ala
655                 660                 665                 670

AAG AAA GCG GTG GCG AGC TTG TTT ACA CGT ACA AGG GAC GGA TTA CAG   2725
Lys Lys Ala Val Ala Ser Leu Phe Thr Arg Thr Arg Asp Gly Leu Gln
                675                 680                 685

GTA AAT GTG ACA GAT TAT CAA GTG GAC CAA GCG GCA AAT TTA GTG TCA   2773
Val Asn Val Thr Asp Tyr Gln Val Asp Gln Ala Ala Asn Leu Val Ser
            690                 695                 700

TGC TTA TCC GAT GAA CAA TAT GGG CAT GAC AAA AAG ATG TTA TTG GAA   2821
Cys Leu Ser Asp Glu Gln Tyr Gly His Asp Lys Lys Met Leu Leu Glu
        705                 710                 715

GCG GTA AGA GCG GCA AAA CGC CTC AGC CGC GAA CGC AAC TTA CTT CAA   2869
Ala Val Arg Ala Ala Lys Arg Leu Ser Arg Glu Arg Asn Leu Leu Gln
    720                 725                 730

GAT CCA GAT TTT AAT ACA ATC AAT AGT ACA GAA GAG AAT GGC TGG AAG   2917
Asp Pro Asp Phe Asn Thr Ile Asn Ser Thr Glu Glu Asn Gly Trp Lys
735                 740                 745                 750

GCA AGT AAC GGT GTT ACT ATT AGC GAG GGC GGT CCA TTC TTT AAA GGT   2965
Ala Ser Asn Gly Val Thr Ile Ser Glu Gly Gly Pro Phe Phe Lys Gly
                755                 760                 765

CGT GCA CTT CAG TTA GCA AGC GCA AGA GAA AAT TAT CCA ACA TAC ATT   3013
Arg Ala Leu Gln Leu Ala Ser Ala Arg Glu Asn Tyr Pro Thr Tyr Ile
            770                 775                 780

TAT CAA AAA GTA GAT GCA TCG GTG TTA AAG CCT TAT ACA CGC TAT AGA   3061
Tyr Gln Lys Val Asp Ala Ser Val Leu Lys Pro Tyr Thr Arg Tyr Arg
        785                 790                 795

CTA GAT GGA TTT GTG AAG AGT AGT CAA GAT TTA GAA ATT GAT CTC ATC   3109
Leu Asp Gly Phe Val Lys Ser Ser Gln Asp Leu Glu Ile Asp Leu Ile
    800                 805                 810

CAC CAT CAT AAA GTC CAT CTT GTA AAA AAT GTA CCA GAT AAT TTA GTA   3157
His His His Lys Val His Leu Val Lys Asn Val Pro Asp Asn Leu Val
815                 820                 825                 830

TCT GAT ACT TAC TCA GAT GGT TCT TGC AGC GGA ATC AAC CGT TGT GAT   3205
Ser Asp Thr Tyr Ser Asp Gly Ser Cys Ser Gly Ile Asn Arg Cys Asp
                835                 840                 845

GAA CAG CAT CAG GTA GAT ATG CAG CTA GAT GCG GAG CAT CAT CCA ATG   3253
Glu Gln His Gln Val Asp Met Gln Leu Asp Ala Glu His His Pro Met
            850                 855                 860

GAT TGC TGT GAA GCG GCT CAA ACA CAT GAG TTT TCT TCC TAT ATT AAT   3301
Asp Cys Cys Glu Ala Ala Gln Thr His Glu Phe Ser Ser Tyr Ile Asn
        865                 870                 875

ACA GGG GAT CTA AAT GCA AGT GTA GAT CAG GGC ATT TGG GTT GTA TTA   3349
Thr Gly Asp Leu Asn Ala Ser Val Asp Gln Gly Ile Trp Val Val Leu
    880                 885                 890
```

-continued

```
AAA GTT CGA ACA ACA GAT GGG TAT GCG ACG TTA GGA AAT CTT GAA TTG    3397
Lys Val Arg Thr Thr Asp Gly Tyr Ala Thr Leu Gly Asn Leu Glu Leu
895                 900                 905                 910

GTA GAG GTT GGG CCA TTA TCG GGT GAA TCT CTA GAA CGG GAA CAA AGA    3445
Val Glu Val Gly Pro Leu Ser Gly Glu Ser Leu Glu Arg Glu Gln Arg
                915                 920                 925

GAT AAT GCG AAA TGG AAT GCA GAG CTA GGA AGA AAA CGT GCA GAA ATA    3493
Asp Asn Ala Lys Trp Asn Ala Glu Leu Gly Arg Lys Arg Ala Glu Ile
            930                 935                 940

GAT CGT GTG TAT TTA GCT GCG AAA CAA GCA ATT AAT CAT CTG TTT GTA    3541
Asp Arg Val Tyr Leu Ala Ala Lys Gln Ala Ile Asn His Leu Phe Val
        945                 950                 955

GAC TAT CAA GAT CAA CAA TTA AAT CCA GAA ATT GGG CTA GCA GAA ATT    3589
Asp Tyr Gln Asp Gln Gln Leu Asn Pro Glu Ile Gly Leu Ala Glu Ile
    960                 965                 970

AAT GAA GCT TCA AAT CTT GTA GAG TCA ATT TCG GGT GTA TAT AGT GAT    3637
Asn Glu Ala Ser Asn Leu Val Glu Ser Ile Ser Gly Val Tyr Ser Asp
975                 980                 985                 990

ACA CTA TTA CAG ATT CCT GGG ATT AAC TAC GAA ATT TAC ACA GAG TTA    3685
Thr Leu Leu Gln Ile Pro Gly Ile Asn Tyr Glu Ile Tyr Thr Glu Leu
                995                1000                1005

TCC GAT CGC TTA CAA CAA GCA TCG TAT CTG TAT ACG TCT AGA AAT GCG    3733
Ser Asp Arg Leu Gln Gln Ala Ser Tyr Leu Tyr Thr Ser Arg Asn Ala
           1010                1015                1020

GTG CAA AAT GGA GAC TTT AAC AGT GGT CTA GAT AGT TGG AAT ACA ACT    3781
Val Gln Asn Gly Asp Phe Asn Ser Gly Leu Asp Ser Trp Asn Thr Thr
       1025                1030                1035

ATG GAT GCA TCG GTT CAG CAA GAT GGC AAT ATG CAT TTC TTA GTT CTT    3829
Met Asp Ala Ser Val Gln Gln Asp Gly Asn Met His Phe Leu Val Leu
   1040                1045                1050

TCG CAT TGG GAT GCA CAA GTT TCC CAA CAA TTG AGA GTA AAT CCG AAT    3877
Ser His Trp Asp Ala Gln Val Ser Gln Gln Leu Arg Val Asn Pro Asn
1055                1060                1065                1070

TGT AAG TAT GTC TTA CGT GTG ACA GCA AGA AAA GTA GGA GGC GGA GAT    3925
Cys Lys Tyr Val Leu Arg Val Thr Ala Arg Lys Val Gly Gly Gly Asp
               1075                1080                1085

GGA TAC GTC ACA ATC CGA GAT GGC GCT CAT CAC CAA GAA ACT CTT ACA    3973
Gly Tyr Val Thr Ile Arg Asp Gly Ala His His Gln Glu Thr Leu Thr
           1090                1095                1100

TTT AAT GCA TGT GAC TAC GAT GTA AAT GGT ACG TAT GTC AAT GAC AAT    4021
Phe Asn Ala Cys Asp Tyr Asp Val Asn Gly Thr Tyr Val Asn Asp Asn
       1105                1110                1115

TCG TAT ATA ACA GAA GAA GTG GTA TTC TAC CCA GAG ACA AAA CAT ATG    4069
Ser Tyr Ile Thr Glu Glu Val Val Phe Tyr Pro Glu Thr Lys His Met
   1120                1125                1130

TGG GTA GAG GTG AGT GAA TCC GAA GGT TCA TTC TAT ATA GAC AGT ATT    4117
Trp Val Glu Val Ser Glu Ser Glu Gly Ser Phe Tyr Ile Asp Ser Ile
1135                1140                1145                1150

GAG TTT ATT GAA ACA CAA GAG TAG AAGAGGGGGA TCCTAACGTA TAGCAACTAT    4171
Glu Phe Ile Glu Thr Gln Glu  *
               1155

GAGAGGATAC TCCGTACAAA CAAAGATTAA AAAAAGGTAA AATGAATAGA ACCCCCTACT    4231

GGTAGAAGGA CCGATAGGGG GTTCTTACAT GAAAAAATGT AGCTGTTTAC TAAGGTGTAT    4291

AAAAAACAGC ATATCTGATA GAAAAAAGTG AGTACCTTAT AAAGAAAGAA TTC          4344
```

( 2 ) INFORMATION FOR SEQ ID NO: 5:

( i ) SEQUENCE CHARACTERISTICS:

( A ) LENGTH: 1157 amino acids ( B ) TYPE: amino acid
( D ) TOPOLOGY: linear ( i i ) MOLECULE TYPE: protein ( x i ) SEQUENCE DESCRIPTION: SEQ ID NO: 5:

Met Asn Arg Asn Asn Gln Asn Glu Tyr Glu Ile Ile Asp Ala Pro His
1 5 10 15

Cys Gly Cys Pro Ser Asp Asp Asp Val Arg Tyr Pro Leu Ala Ser Asp
20 25 30

Pro Asn Ala Ala Leu Gln Asn Met Asn Tyr Lys Asp Tyr Leu Gln Met
35 40 45

Thr Asp Glu Asp Tyr Thr Asp Ser Tyr Ile Asn Pro Ser Leu Ser Ile
50 55 60

Ser Gly Arg Asp Ala Val Gln Thr Ala Leu Thr Val Val Gly Arg Ile
65 70 75 80

Leu Gly Ala Leu Gly Val Pro Phe Ser Gly Gln Ile Val Ser Phe Tyr
85 90 95

Gln Phe Leu Leu Asn Thr Leu Trp Pro Val Asn Asp Thr Ala Ile Trp
100 105 110

Glu Ala Phe Met Arg Gln Val Glu Glu Leu Val Asn Gln Gln Ile Thr
115 120 125

Glu Phe Ala Arg Asn Gln Ala Leu Ala Arg Leu Gln Gly Leu Gly Asp
130 135 140

Ser Phe Asn Val Tyr Gln Arg Ser Leu Gln Asn Trp Leu Ala Asp Arg
145 150 155 160

Asn Asp Thr Arg Asn Leu Ser Val Val Arg Ala Gln Phe Ile Ala Leu
165 170 175

Asp Leu Asp Phe Val Asn Ala Ile Pro Leu Phe Ala Val Asn Gly Gln
180 185 190

Gln Val Pro Leu Leu Ser Val Tyr Ala Gln Ala Val Asn Leu His Leu
195 200 205

Leu Leu Leu Lys Asp Ala Ser Leu Phe Gly Glu Gly Trp Gly Phe Thr
210 215 220

Gln Gly Glu Ile Ser Thr Tyr Tyr Asp Arg Gln Leu Glu Leu Thr Ala
225 230 235 240

Lys Tyr Thr Asn Tyr Cys Glu Thr Trp Tyr Asn Thr Gly Leu Asp Arg
245 250 255

Leu Arg Gly Thr Asn Thr Glu Ser Trp Leu Arg Tyr His Gln Phe Arg
260 265 270

Arg Glu Met Thr Leu Val Val Leu Asp Val Val Ala Leu Phe Pro Tyr
275 280 285

Tyr Asp Val Arg Leu Tyr Pro Thr Gly Ser Asn Pro Gln Leu Thr Arg
290 295 300

Glu Val Tyr Thr Asp Pro Ile Val Phe Asn Pro Pro Ala Asn Val Gly
305 310 315 320

Leu Cys Arg Arg Trp Gly Thr Asn Pro Tyr Asn Thr Phe Ser Glu Leu
325 330 335

Glu Asn Ala Phe Ile Arg Pro Pro His Leu Phe Asp Arg Leu Asn Ser
340 345 350

Leu Thr Ile Ser Ser Asn Arg Phe Pro Val Ser Ser Asn Phe Met Asp
355 360 365

Tyr Trp Ser Gly His Thr Leu Arg Arg Ser Tyr Leu Asn Asp Ser Ala
370 375 380

Val Gln Glu Asp Ser Tyr Gly Leu Ile Thr Thr Thr Arg Ala Thr Ile

-continued 385 390 395 400

Asn Pro Gly Val Asp Gly Thr Asn Arg Ile Glu Ser Thr Ala Val Asp
405 410 415

Phe Arg Ser Ala Leu Ile Gly Ile Tyr Gly Val Asn Arg Ala Ser Phe
420 425 430

Val Pro Gly Gly Leu Phe Asn Gly Thr Thr Ser Pro Ala Asn Gly Gly
435 440 445

Cys Arg Asp Leu Tyr Asp Thr Asn Asp Glu Leu Pro Pro Asp Glu Ser
450 455 460

Thr Gly Ser Ser Thr His Arg Leu Ser His Val Thr Phe Phe Ser Phe
465 470 475 480

Gln Thr Asn Gln Ala Gly Ser Ile Ala Asn Ala Gly Ser Val Pro Thr
485 490 495

Tyr Val Trp Thr Arg Arg Asp Val Asp Leu Asn Asn Thr Ile Thr Pro
500 505 510

Asn Arg Ile Thr Gln Leu Pro Leu Val Lys Ala Ser Ala Pro Val Ser
515 520 525

Gly Thr Thr Val Leu Lys Gly Pro Gly Phe Thr Gly Gly Gly Ile Leu
530 535 540

Arg Arg Thr Thr Asn Gly Thr Phe Gly Thr Leu Arg Val Thr Val Asn
545 550 555 560

Ser Pro Leu Thr Gln Gln Tyr Arg Leu Arg Val Arg Phe Ala Ser Thr
565 570 575

Gly Asn Phe Ser Ile Arg Val Leu Arg Gly Gly Val Ser Ile Gly Asp
580 585 590

Val Arg Leu Gly Ser Thr Met Asn Arg Gly Gln Glu Leu Thr Tyr Glu
595 600 605

Ser Phe Phe Thr Arg Glu Phe Thr Thr Thr Gly Pro Phe Asn Pro Pro
610 615 620

Phe Thr Phe Thr Gln Ala Gln Glu Ile Leu Thr Val Asn Ala Glu Gly
625 630 635 640

Val Ser Thr Gly Gly Glu Tyr Tyr Ile Asp Arg Ile Glu Ile Val Pro
645 650 655

Val Asn Pro Ala Arg Glu Ala Glu Glu Asp Leu Glu Ala Ala Lys Lys
660 665 670

Ala Val Ala Ser Leu Phe Thr Arg Thr Arg Asp Gly Leu Gln Val Asn
675 680 685

Val Thr Asp Tyr Gln Val Asp Gln Ala Ala Asn Leu Val Ser Cys Leu
690 695 700

Ser Asp Glu Gln Tyr Gly His Asp Lys Lys Met Leu Leu Glu Ala Val
705 710 715 720

Arg Ala Ala Lys Arg Leu Ser Arg Glu Arg Asn Leu Leu Gln Asp Pro
725 730 735

Asp Phe Asn Thr Ile Asn Ser Thr Glu Glu Asn Gly Trp Lys Ala Ser
740 745 750

Asn Gly Val Thr Ile Ser Glu Gly Gly Pro Phe Phe Lys Gly Arg Ala
755 760 765

Leu Gln Leu Ala Ser Ala Arg Glu Asn Tyr Pro Thr Tyr Ile Tyr Gln
770 775 780

Lys Val Asp Ala Ser Val Leu Lys Pro Tyr Thr Arg Tyr Arg Leu Asp
785 790 795 800

Gly Phe Val Lys Ser Ser Gln Asp Leu Glu Ile Asp Leu Ile His His
805 810 815

-continued

| | | | | | | | | | | | | | | | |
|---|---|---|---|---|---|---|---|---|---|---|---|---|---|---|---|
| His | Lys | Val | His | Leu | Val | Lys | Asn | Val | Pro | Asp | Asn | Leu | Val | Ser | Asp |
| | | | 820 | | | | | 825 | | | | | 830 | | |
| Thr | Tyr | Ser | Asp | Gly | Ser | Cys | Ser | Gly | Ile | Asn | Arg | Cys | Asp | Glu | Gln |
| | | 835 | | | | | 840 | | | | | 845 | | | |
| His | Gln | Val | Asp | Met | Gln | Leu | Asp | Ala | Glu | His | His | Pro | Met | Asp | Cys |
| | 850 | | | | | 855 | | | | | 860 | | | | |
| Cys | Glu | Ala | Ala | Gln | Thr | His | Glu | Phe | Ser | Ser | Tyr | Ile | Asn | Thr | Gly |
| 865 | | | | | 870 | | | | | 875 | | | | | 880 |
| Asp | Leu | Asn | Ala | Ser | Val | Asp | Gln | Gly | Ile | Trp | Val | Val | Leu | Lys | Val |
| | | | | 885 | | | | | 890 | | | | | 895 | |
| Arg | Thr | Thr | Asp | Gly | Tyr | Ala | Thr | Leu | Gly | Asn | Leu | Glu | Leu | Val | Glu |
| | | | 900 | | | | | 905 | | | | | 910 | | |
| Val | Gly | Pro | Leu | Ser | Gly | Glu | Ser | Leu | Glu | Arg | Glu | Gln | Arg | Asp | Asn |
| | | 915 | | | | | 920 | | | | | 925 | | | |
| Ala | Lys | Trp | Asn | Ala | Glu | Leu | Gly | Arg | Lys | Arg | Ala | Glu | Ile | Asp | Arg |
| | 930 | | | | | 935 | | | | | 940 | | | | |
| Val | Tyr | Leu | Ala | Ala | Lys | Gln | Ala | Ile | Asn | His | Leu | Phe | Val | Asp | Tyr |
| 945 | | | | | 950 | | | | | 955 | | | | | 960 |
| Gln | Asp | Gln | Gln | Leu | Asn | Pro | Glu | Ile | Gly | Leu | Ala | Glu | Ile | Asn | Glu |
| | | | | 965 | | | | | 970 | | | | | 975 | |
| Ala | Ser | Asn | Leu | Val | Glu | Ser | Ile | Ser | Gly | Val | Tyr | Ser | Asp | Thr | Leu |
| | | | 980 | | | | | 985 | | | | | 990 | | |
| Leu | Gln | Ile | Pro | Gly | Ile | Asn | Tyr | Glu | Ile | Tyr | Thr | Glu | Leu | Ser | Asp |
| | | 995 | | | | | 1000 | | | | | 1005 | | | |
| Arg | Leu | Gln | Gln | Ala | Ser | Tyr | Leu | Tyr | Thr | Ser | Arg | Asn | Ala | Val | Gln |
| | 1010 | | | | | 1015 | | | | | 1020 | | | | |
| Asn | Gly | Asp | Phe | Asn | Ser | Gly | Leu | Asp | Ser | Trp | Asn | Thr | Thr | Met | Asp |
| 1025 | | | | | 1030 | | | | | 1035 | | | | | 1040 |
| Ala | Ser | Val | Gln | Gln | Asp | Gly | Asn | Met | His | Phe | Leu | Val | Leu | Ser | His |
| | | | | 1045 | | | | | 1050 | | | | | 1055 | |
| Trp | Asp | Ala | Gln | Val | Ser | Gln | Gln | Leu | Arg | Val | Asn | Pro | Asn | Cys | Lys |
| | | | 1060 | | | | | 1065 | | | | | 1070 | | |
| Tyr | Val | Leu | Arg | Val | Thr | Ala | Arg | Lys | Val | Gly | Gly | Gly | Asp | Gly | Tyr |
| | | 1075 | | | | | 1080 | | | | | 1085 | | | |
| Val | Thr | Ile | Arg | Asp | Gly | Ala | His | His | Gln | Glu | Thr | Leu | Thr | Phe | Asn |
| | 1090 | | | | | 1095 | | | | | 1100 | | | | |
| Ala | Cys | Asp | Tyr | Asp | Val | Asn | Gly | Thr | Tyr | Val | Asn | Asp | Asn | Ser | Tyr |
| 1105 | | | | | 1110 | | | | | 1115 | | | | | 1120 |
| Ile | Thr | Glu | Glu | Val | Val | Phe | Tyr | Pro | Glu | Thr | Lys | His | Met | Trp | Val |
| | | | | 1125 | | | | | 1130 | | | | | 1135 | |
| Glu | Val | Ser | Glu | Ser | Glu | Gly | Ser | Phe | Tyr | Ile | Asp | Ser | Ile | Glu | Phe |
| | | | 1140 | | | | | 1145 | | | | | 1150 | | |
| Ile | Glu | Thr | Gln | Glu | | | | | | | | | | | |
| | | 1155 | | | | | | | | | | | | | |

What is claimed is:

1. A biologically pure culture of a bacterium selected from the group of: the BTS02617A strain of BCCM-LMG deposit number P-12592, the BTS02618A strain of BCCM-LMG deposit number P-12593, the BTS02654B strain of BCCM-LMG deposit number P-12594 and the BTS02652E strain of BCCM-LMG deposit number P-13493.

2. A crystal or a crystal-spore mixture of a biologically pure culture of a bacterium selected from the group of: the BTS02617A strain of BCCM-LMG deposit number P-12592, the BTS02618A strain of BCCM-LMG deposit number P-12593, the BTS02654B strain of BCCM-LMG deposit number P-12594 and the BTS02652E strain of BCCM-LMG deposit number P-13493.

3. A recombinantly produced protein comprising an amino acid sequence of SEQ ID NO: 5 or an insecticidally effective fragment thereof.

4. The protein of claim 3, comprising the amino acid sequence of SEQ ID NO: 5 from amino acid position 44 to amino acid position 658.

5. The protein of claim 3, comprising the amino acid sequence of SEQ ID NO: 5 from amino acid position 165 to amino acid position 658.

6. The protein of claim 3, comprising the amino acid sequence of SEQ ID NO: 5 from amino acid position 44 to amino acid position 658 and further comprising an amino acid sequence of a selectable marker protein.

7. The protein of claim 3, which is produced in cells of a plant.

8. An isolated DNA encoding the protein of claim 3.

9. An isolated DNA encoding the protein of claim 4 or 5.

10. An isolated DNA comprising a nucleotide sequence encoding the protein of SEQ ID NO: 5 from amino acid position 44 to amino acid position 658 or an insecticidally effective portion thereof.

11. The DNA of claim 8, comprising the nucleotide sequence of SEQ ID NO: 4 from nucleotide position 797 to nucleotide position 2641.

12. A chimeric gene, comprising:

a) the DNA of any one of claims 8, 10, or 11, and b) a promoter region capable of transcribing said DNA in a plant cell.

13. A chimeric gene, comprising:

a) the DNA of claim 9, and b) a promoter region capable of transcribing said DNA in a plant cell.

14. The chimeric gene of claim 12, wherein said DNA is fused to a DNA encoding a selectable marker protein.

15. The chimeric gene of claim 13, wherein said DNA is fused to a DNA encoding a selectable marker protein.

16. An insecticidal composition against Lepidoptera comprising an active ingredient selected from the group consisting of: the bacterium of claim 1, the crystal or crystal-spore mixture of claim 2, and the protein of claim 3.

17. A transformed microorganism, comprising the DNA of claim 8.

18. A process for controlling an insect pest characterized by the step of contacting the pest with the composition of claim 16.

19. A process for controlling an insect pest, comprising the step of contacting said pest with a protein selected from:

a) an insecticidal protein comprising the amino acid sequence of SEQ ID NO: 5 from amino acid position 44 to amino acid position 658; and b) an insecticidal protein comprising the amino acid sequence of SEQ ID NO: 5 from amino acid position 165 to amino acid position 658.

20. The process of claim 19, wherein said contacting step is by expression of a DNA encoding said insecticidal protein in cells of a plant.

21. An isolated DNA encoding the protein of claim 3 having a modified codon usage.

22. An isolated DNA encoding the protein of claim 4 or 5 having a modified codon usage.

23. An isolated DNA comprising a nucleotide sequence encoding the protein of SEQ ID NO: 5 from amino acid position 44 to amino acid position 658 or an insecticidally effective portion thereof, wherein said artificial DNA has modified codon usage.

* * * * *

UNITED STATES PATENT AND TRADEMARK OFFICE

CERTIFICATE OF CORRECTION

PATENT NO. : 5,885,571

DATED : March 23, 1999

INVENTOR(S) : Bart Lambert, et al.

It is certified that error appears in the above-identified patent and that said Letters Patent is hereby corrected as shown below:

Column 9, line 4, change "FIG. 1" to --The sole figure shows--.

Signed and Sealed this

Fifteenth Day of June, 1999

Attest:

Q. TODD DICKINSON

Attesting Officer

*Acting Commissioner of Patents and Trademarks*